US009688965B2

(12) United States Patent
Wu et al.

(10) Patent No.: US 9,688,965 B2
(45) Date of Patent: Jun. 27, 2017

(54) RECOMBINANT NEURAMINIDASE AND USES THEREOF

(71) Applicant: National Tsing Hua University, Hsinchu (TW)

(72) Inventors: Suh-Chin Wu, Hsinchu (TW); Wen-Chun Liu, Hsinchu (TW); Chia-Ying Lin, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 37 days.

(21) Appl. No.: 14/685,286

(22) Filed: Apr. 13, 2015

(65) Prior Publication Data

US 2016/0067328 A1 Mar. 10, 2016

(30) Foreign Application Priority Data

Sep. 4, 2014 (TW) ............................. 103130669 A

(51) Int. Cl.

*A61K 39/12* (2006.01)
*C12N 7/00* (2006.01)
*C12N 9/24* (2006.01)
*C07K 14/005* (2006.01)
*A61K 39/00* (2006.01)

(52) U.S. Cl.

CPC ................ *C12N 7/00* (2013.01); *A61K 39/12* (2013.01); *C07K 14/005* (2013.01); *C12N 9/2402* (2013.01); *A61K 2039/5258* (2013.01); *A61K 2039/55511* (2013.01); *A61K 2039/55561* (2013.01); *A61K 2039/6093* (2013.01); *C12N 2760/16121* (2013.01); *C12N 2760/16122* (2013.01); *C12N 2760/16123* (2013.01); *C12N 2760/16134* (2013.01)

(58) Field of Classification Search

None

See application file for complete search history.

*Primary Examiner* — Janet L Andres
*Assistant Examiner* — Stuart W Snyder
(74) *Attorney, Agent, or Firm* — Muncy, Geissler, Olds & Lowe, P.C.

(57) ABSTRACT

A recombinant neuraminidase based on amino acid sequence (SEQ ID NO: 1) of wild-type pH1N1-NA (A/Texas/05/2009) influenza virus is provided. The recombinant neuraminidase of the present invention has an ectodomain with an amino acid sequence identical to SEQ ID NO: 1 and replaced at specific positions 149, 344, 365 and 366 residue(s) with corresponding amino acids of other influenza viruses. The recombinant neuraminidase may incur cross-protective immunity and be used as universal influenza vaccine.

13 Claims, 17 Drawing Sheets

| | Km (μg/mL) | V max |
|---|---|---|
| H5N1-rNA | 2.80 | 0.35 |
| pH1N1-rNA | 1.90 | 0.30 |

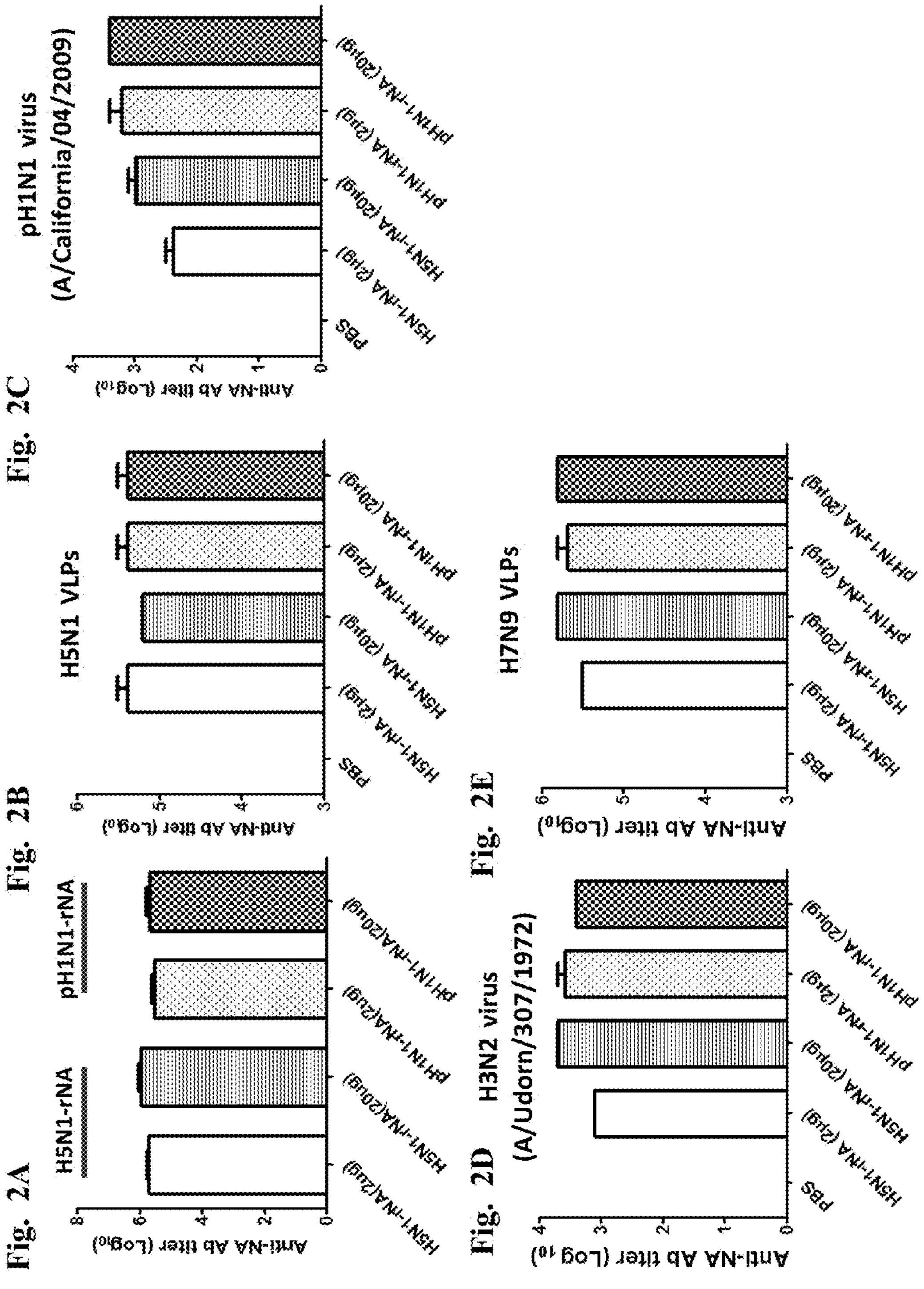
Fig. 2A
H5N1-rNA
pH1N1-rNA
Anti-NA Ab titer (Log10)
0
2
4
6
8
H5N1-rNA(2ug)
H5N1-rNA(20ug)
pH1N1-rNA(2ug)
pH1N1-rNA(20ug)
Fig. 2B
H5N1 VLPs
Anti-NA Ab titer (Log10)
3
4
5
6
PBS
H5N1-rNA (2µg)
H5N1-rNA (20µg)
pH1N1-rNA (2µg)
pH1N1-rNA (20µg)
Fig. 2C
pH1N1 virus
(A/California/04/2009)
Anti-NA Ab titer (Log10)
0
1
2
3
4
PBS
H5N1-rNA (2µg)
H5N1-rNA (20µg)
pH1N1-rNA (2µg)
pH1N1-rNA (20µg)
Fig. 2D
H3N2 virus
(A/Udorn/307/1972)
Anti-NA Ab titer (Log10)
0
1
2
3
4
PBS
H5N1-rNA (2µg)
H5N1-rNA (20µg)
pH1N1-rNA (2µg)
pH1N1-rNA (20µg)
Fig. 2E
H7N9 VLPs
Anti-NA Ab titer (Log10)
3
4
5
6
PBS
H5N1-rNA (2µg)
H5N1-rNA (20µg)
pH1N1-rNA (2µg)
pH1N1-rNA (20µg)

H5N1 challenge pH1N1 challenge pH1N1 challenge

H5N1 challenge

H7N9 challenge

Fig. 8

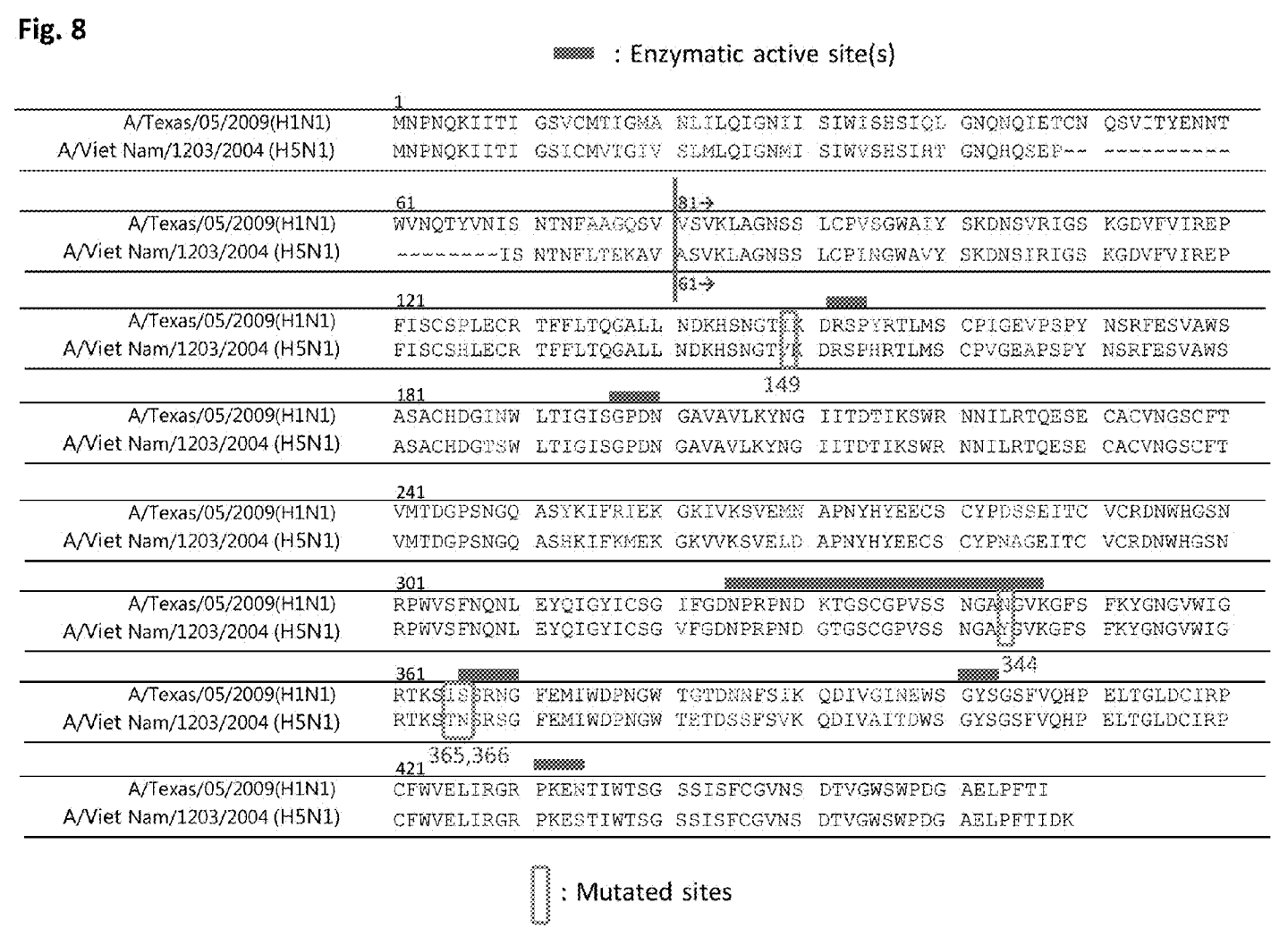

▒ : Enzymatic active site(s)

| | | | | | | |
|---|---|---|---|---|---|---|
| | 1 | | | | | |
| A/Texas/05/2009(H1N1) | MNPNQKIITI | GSVCMTIGMA | NLILQIGNII | SIWISHSIQL | GNQNQIETCN | QSVITYENNT |
| A/Viet Nam/1203/2004 (H5N1) | MNPNQKIITI | GSICMVTGIV | SLMLQIGNMI | SIWVSHSIHT | GNQHQSEP-- | ---------- |
| | 61 | | 81→ | | | |
| A/Texas/05/2009(H1N1) | WVNQTYVNIS | NTNFAAGQSV | VSVKLAGNSS | LCPVSGWAIY | SKDNSVRIGS | KGDVFVIREP |
| A/Viet Nam/1203/2004 (H5N1) | ---------IS | NTNFLTEKAV | ASVKLAGNSS | LCPINGWAVY | SKDNSIRIGS | KGDVFVIREP |
| | 121 | | 61→ | | | |
| A/Texas/05/2009(H1N1) | FISCSPLECR | TFFLTQGALL | NDKHSNGTIK | DRSPYRTLMS | CPIGEVPSPY | NSRFESVAWS |
| A/Viet Nam/1203/2004 (H5N1) | FISCSHLECR | TFFLTQGALL | NDKHSNGTVK | DRSPHRTLMS | CPVGEAPSPY | NSRFESVAWS |
| | | | 149 | | | |
| | 181 | | | | | |
| A/Texas/05/2009(H1N1) | ASACHDGINW | LTIGISGPDN | GAVAVLKYNG | IITDTIKSWR | NNILRTQESE | CACVNGSCFT |
| A/Viet Nam/1203/2004 (H5N1) | ASACHDGTSW | LTIGISGPDN | GAVAVLKYNG | IITDTIKSWR | NNILRTQESE | CACVNGSCFT |
| | 241 | | | | | |
| A/Texas/05/2009(H1N1) | VMTDGPSNGQ | ASYKIFRIEK | GKIVKSVEMN | APNYHYEECS | CYPDSSEITC | VCRDNWHGSN |
| A/Viet Nam/1203/2004 (H5N1) | VMTDGPSNGQ | ASHKIFKMEK | GKVVKSVELD | APNYHYEECS | CYPNAGEITC | VCRDNWHGSN |
| | 301 | | | | | |
| A/Texas/05/2009(H1N1) | RPWVSFNQNL | EYQIGYICSG | IFGDNPRPND | KTGSCGPVSS | NGANGVKGFS | FKYGNGVWIG |
| A/Viet Nam/1203/2004 (H5N1) | RPWVSFNQNL | EYQIGYICSG | VFGDNPRPND | GTGSCGPVSS | NGAYGVKGFS | FKYGNGVWIG |
| | 361 | | | | 344 | |
| A/Texas/05/2009(H1N1) | RTKSISSRNG | FEMIWDPNGW | TGTDNNFSIK | QDIVGINEWS | GYSGSFVQHP | ELTGLDCIRP |
| A/Viet Nam/1203/2004 (H5N1) | RTKSTNSRSG | FEMIWDPNGW | TETDSSFSVK | QDIVAITDWS | GYSGSFVQHP | ELTGLDCIRP |
| | 421 365,366 | | | | | |
| A/Texas/05/2009(H1N1) | CFWVELIRGR | PKENTIWTSG | SSISFCGVNS | DTVGWSWPDG | AELPFTI | |
| A/Viet Nam/1203/2004 (H5N1) | CFWVELIRGR | PKESTIWTSG | SSISFCGVNS | DTVGWSWPDG | AELPFTIDK | |

▯ : Mutated sites

2μg pH1N1

H5N1

H3N2

H7N9
NA inhibition (%)
Sera dilution (Log10)
PBS
pH1N1-rNA (wild-type)
pH1N1-rNA (I149V)
pH1N1-rNA (N344Y)
pH1N1-rNA (I365T/S366N)

Fig.12A Amino acid alignments of different groups neuraminidase (NA)

Enzyme active site(s)

```
Positions from 1 till 60
         Consensus sequence           MNPNQKIITIGSVCMTIGAIALLLQIANLISIWISHSIHLGNQECDEPANQPVITCENIT
ACU13061 A/Texas/05/2009(H1N1)        ..................MAN.I...G.I.........Q....NQI.TC..S...Y..N.
ABP52008 A/Viet Nam/1203/2004(H5N1)   ............I..VT.IVS.M...G.M....V.....T...HQS..-----------
ABF21339 A/Udorn/307/1972(H3N2)       .............SL..AT.CF.M...I.V---TTVTL.FKOY...S...RO.MP..F.I
AGL44440 A/Shanghai/02/2013(H7N9)    .......LCTSATAII.....V.IGM...G---LNIGL..KP-G.NCSHS..ET.NTSQ.

Positions from 61 till 120
         Consensus sequence           IENNIYEEISNTNFAAEKAVASVKLAGNNLSKSLCPINGWAIYSKDNSIRIGSKGDVFVI
ACU13061 A/Texas/05/2009(H1N1)        WV.QT.VN........GQS.V.......S---....VS..........V...........
ABP52008 A/Viet Nam/1203/2004(H5N1)   --------......LT..............S---..........V...................
ABF21339 A/Udorn/307/1972(H3N2)       ..R..T.IVYL..TTI..EICPKLVEYR.W..PQ.K.T.F.PF.......LSAG..IW.T
AGL44440 A/Shanghai/02/2013(H7N9)    .I..Y.N.TNI..IQK.ERTSR---NF...T.G..T..S.H..G...AV...ESS..L.T

Positions from 121 till 180
                                                                           149
         Consensus sequence           REPFISCDPLECRTFALTQGALLNDKHSNGTIHDRSPHRTLMSCPLGEPPSPYNSRFECI
ACU13061 A/Texas/05/2009(H1N1)        .......S.......F.................K....Y........I..V.........SV
ABP52008 A/Viet Nam/1203/2004(H5N1)   .......SH......F.................VK.............V..A.........SV
ABF21339 A/Udorn/307/1972(H3N2)       ...YV....GK.YQ...G..TT.DN....D.....T.....LMNE..V.FHL-GT.QV..
AGL44440 A/Shanghai/02/2013(H7N9)    ...YV....D...FY..S..TTIRG..........QY.A.I.W..SS..TV....V...

Positions from 181 till 240
         Consensus sequence           AWSASACHDGKSWLTICISGPDNGAVAVLKYNGIITDTIKSWRNNILRTQESECACVNGS
ACU13061 A/Texas/05/2009(H1N1)        ...........IN....G..........................................
ABP52008 A/Viet Nam/1203/2004(H5N1)   ...........T.....G..........................................
ABF21339 A/Udorn/307/1972(H3N2)       ...S.S......A..HV.VT.Y.KN.T.SFI.D.RLV.S.G..SQ..........V.I..T
AGL44440 A/Shanghai/02/2013(H7N9)    G..STS......RMS......N.N.S..VW..RRPVAE.NT.AR..........V.H..V
```

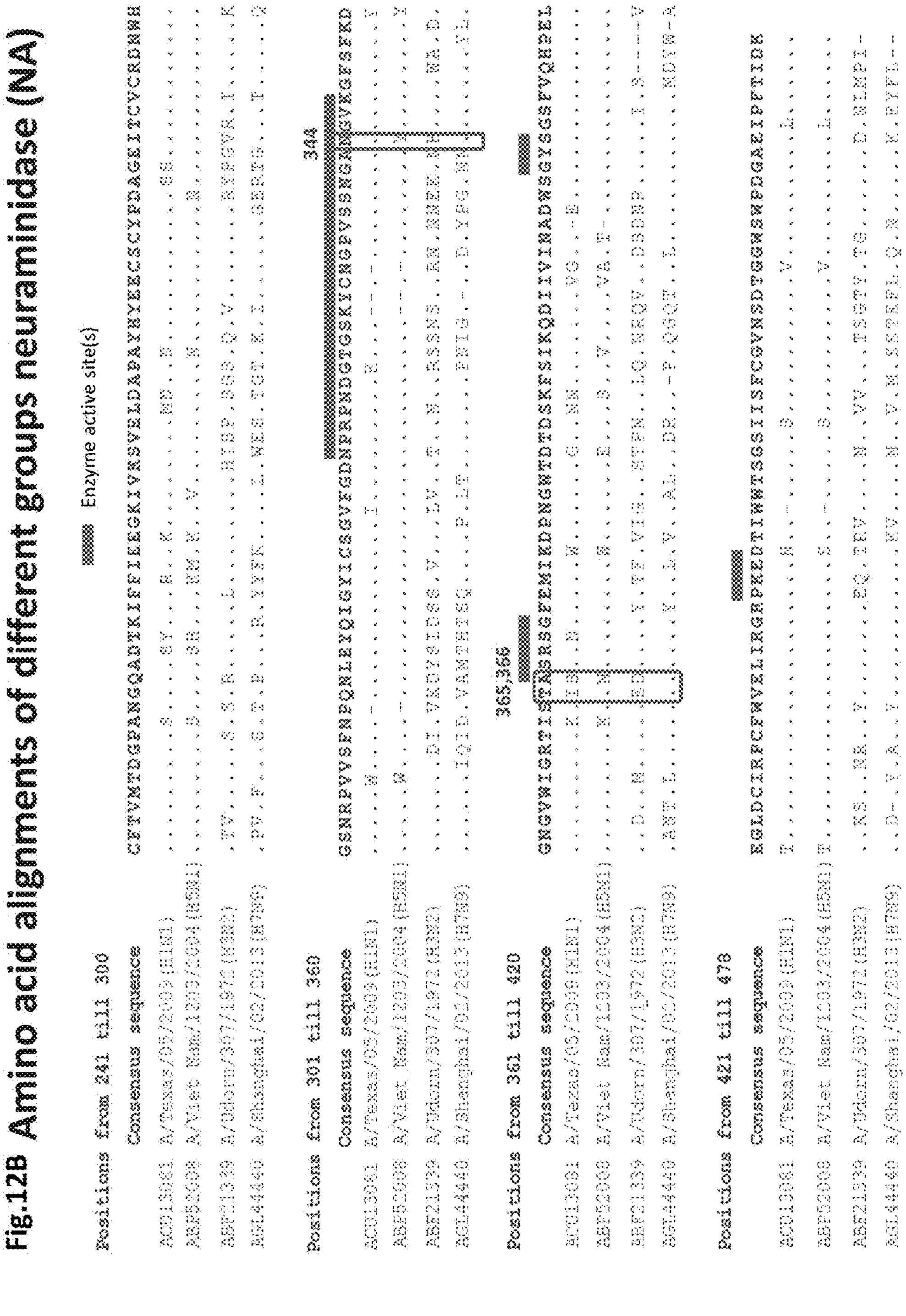
Fig.12B Amino acid alignments of different groups neuraminidase (NA)
Enzyme active site(s)
Positions from 241 till 300
Positions from 301 till 360
Positions from 361 till 420
Positions from 421 till 478
344
365,366

2μg pH1N1

H5N1

H3N2

H7N9
NA Inhibition (%)
Sera dilution (Log10)
PBS
pH1N1-rNA (wild-type)
pH1N1-N344H (N2)
pH1N1-I365T/S366A (N9)

Fig. 15A
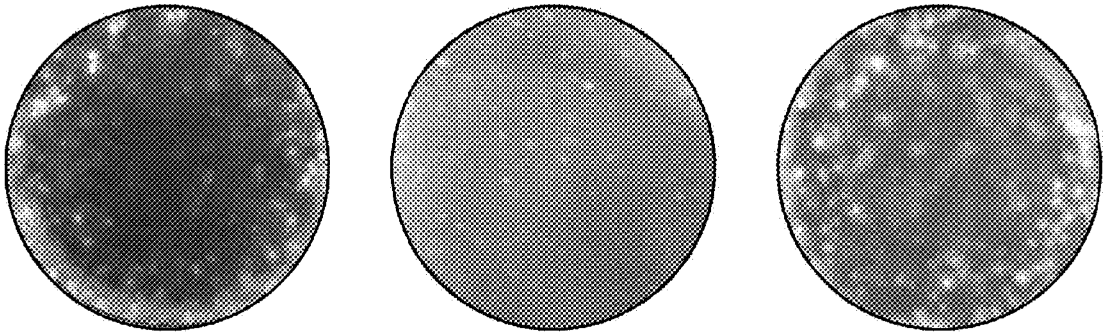
Fig. 15B (MOI : 0.01)
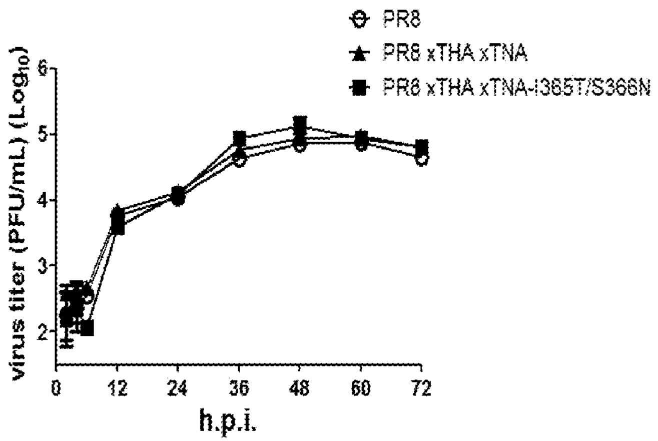
Fig. 15C
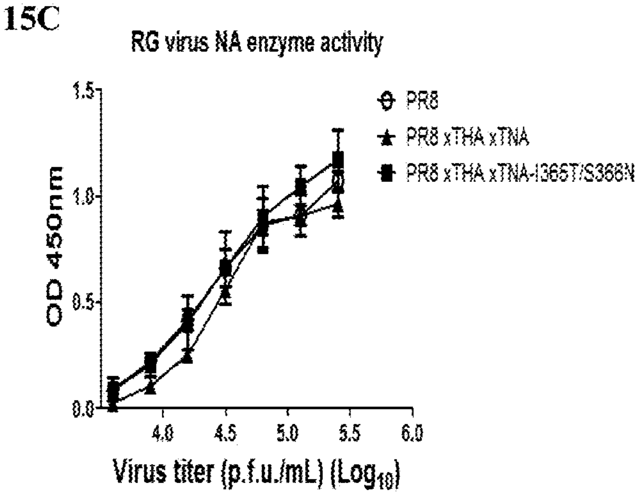

RECOMBINANT NEURAMINIDASE AND USES THEREOF

BACKGROUND OF THE INVENTION

1. Field of the Invention

The present invention relates to recombinant neuraminidase and uses thereof, particularly to recombinant neuraminidase capable of being used as universal influenza vaccine and uses thereof.

2. Description of the Prior Art

Members of the Orthomyxoviridae family, influenza A viruses are enveloped viruses containing a single strand, 8-segment negative sense RNA genome typically encoding 11-12 viral proteins. Influenza A virus subtypes have been classified based on the antigenic properties of hemagglutinin (HA) and neuraminidase (NA) glycoproteins, respectively designated as H1-H16 and N1-N9. One recent report describes H17N10 and H18N11 identified from fruit bats. According to phylogenetic analyses, N1-N9 can be classified as belonging to group 1 (including N1, N4, N5 and N8) or group 2 (including N2, N3, N6, N7 and N9). To date, only N1, N2 and N9 subtypes are known to trigger human epidemics.

NA, an enzymatic protein with a tetrameric complex structure, is capable of cleaving sialic acid linkages on cell surfaces, thereby facilitating viral release from infected cells. NA also contributes to viral transmission and infection by destroying decoy receptors on cilia, mucins, and cellular glycocalyx. NA immunogenicity was first observed in human subjects immunized with a NA-specific inactivated vaccine. The use of recombinant NA (rNA) proteins expressed in yeast or insect cells elicits protection against lethal virus challenges in immunized mice. Ferrets immunized with rNA proteins exhibit a distinctive type of protection in addition to that provided by HA immunization alone. NA-inhibiting (NI) antibodies are known to limit virus spreading and to mitigate clinical symptoms of IAV infection. Mice immunized with a reverse-genetic reassortant H1N1 virus containing seasonal influenza virus NA exhibit cross-reactive NI antibodies and reduced mortality from pH1N1 virus challenges. Live attenuated influenza vaccines (LAIVs) for seasonal H1N1, H3N2 and pH1N1 strains have been reported as inducing cross-reactive NI antibodies to H5N1 viruses in ferrets, and NI antibodies elicited by a seasonal trivalent influenza vaccine have been reported as providing cross-protective immunity against lethal H5N1 challenges, also in ferrets. Further, NA-based virus-like particles (VLPs) containing NA, M1 and M2 have been shown to elicit more potent NI antibodies and to confer cross-protective immunity against H5N1 and pH1N1 viral challenges in mice. NI antibodies have also been detected in humans vaccinated with an H5N1 inactivated vaccine, as well as in humans exposed to natural infections. NA immunogenicity and cross-protective mechanisms remain unclear.

SUMMARY OF THE INVENTION

The present invention is directed to providing a recombinant neuraminidase that may incur cross-protective immunity and be used as universal influenza vaccine.

According to one embodiment of the present invention, a recombinant neuraminidase comprises an ectodomain provided with an amino acid sequence at least 95% identical to SEQ ID NO: 1, wherein the amino acids at positions 365 and 366 is replaced from IS to TN.

According to another embodiment of the present invention, a polynucleotide encoding the above-mentioned recombinant neuraminidase is provided.

According to still another embodiment of the present invention, a recombinant influenza virus comprises the above-mentioned recombinant neuraminidase or polynucleotide encoding the same.

According to yet another embodiment of the present invention, an influenza virus vaccine comprises the above-mentioned recombinant neuraminidase or polynucleotide encoding the same, wherein the influenza virus vaccine may be an inactivated vaccine, an attenuated influenza, a virus-like particle vaccine or a subunit vaccine.

Other advantages of the present invention will become apparent from the following descriptions taken in conjunction with the accompanying drawings wherein certain embodiments of the present invention are set forth by way of illustration and examples.

BRIEF DESCRIPTION OF THE DRAWINGS

The foregoing aspects and many of the accompanying advantages of this invention will become more readily appreciated as the same becomes better understood by reference to the following detailed descriptions, when taken in conjunction with the accompanying drawings, wherein:

FIGS. 2A to 2E illustrate NA-specific IgG antibodies induced by rNA immunization;

FIG. 8 illustrates the mutated sites and comparison result between pH1N1 and H5N1;

FIGS. 12A and 12B illustrate the amino acid alignments of different groups neuraminidase (NA);

FIGS. 15A to 15C illustrate plaque morphologies, virus titers and NA enzymatic activity of PR8 viruses, pH1N1/PR8 viruses, and pH1N1/PR8 viruses with the I365T/S366N mutation.

DESCRIPTION OF THE PREFERRED EMBODIMENT

Figure 1A:
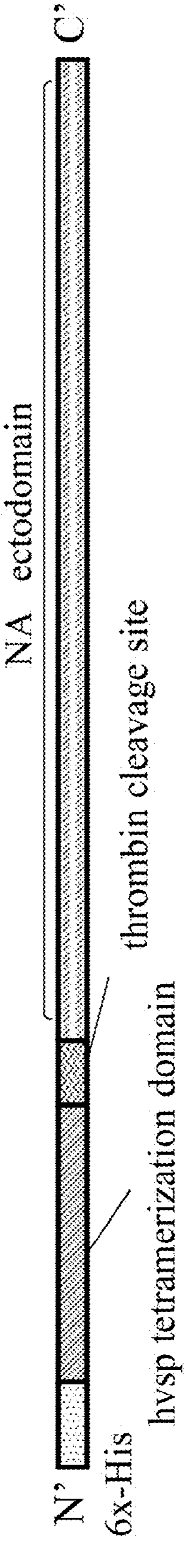
FIGS. 1A to 1D illustrate construction, expression and characterization of soluble recombinant NA (rNA) proteins.

The present invention provides a recombinant neuraminidase, which is based on the sequence list (SEQ ID NO: 1) of emerging wild-type influenza virus pH1N1-NA (A/Texas/05/2009). The recombinant neuraminidase of the present invention comprises an ectodomain provided with an amino acid sequence identical to SEQ ID NO: 1.

Refer to Table 1, which illustrates corresponding amino acids at specific position 149、344、365 and 366 of pH1N1、H5N1、H3N2、H7N9. The present invention is directed to providing substitution at specific positions with corresponding amino acids of H5N1, H3N2, and H7N9 so as to incur cross-protective immunity. To be specific, the amino acid sequence comprises one of the following amino acids: (i) V replacing I at position 149; (ii) Y or H replacing N at position 344; and (iii) TA, TN or ED replacing IS at positions 365 and 366.

TABLE 1

Corresponding amino acids at specific position 149, 344, 365 and 366 of pH1N1, H5N1, H3N2, H7N9

| Strain | Position 149 | 344 | 365, 366 |
|---|---|---|---|
| A/Texas/05/2009(H1N1) | I | N | IS |
| A/Vietnam/1203/2004(H5N1) | V | Y | TN |
| A/Udorn/307/1972(H3N2) | I | H | ED |
| A/Shanghai/02/2013(H7N9) | I | N | TA |

That is, the recombinant neuraminidase of the present invention may obtained by site-directed mutagenesis at mutations of NA gene using a plasmid encoding wild-type pH1N1 gene (SEQ ID NO: 1) as the template.

The sequences of H5N1, H3N2 and H7N9 of the present invention are listed in Seq ID: NO.9; Seq ID: NO.10; Seq ID: NO.11.

It is known that 94.6% of amino acids in the NA ectodomain of influenza virus are conserved. Those skilled in the art of the present invention may appreciate that some amino acids in the NA ectodomain of influenza virus may be replaced without resulting in obvious influences in protein structure or function. Therefore, the recombinant NA ectodomain of the present invention may be provided with an amino acid sequence at least 95%, preferable 97% or 99% identical to SEQ ID NO: 1.

Referring to Table 2, in one specific embodiment, the amino acid sequence of the ectodomain is selected from the group consisting of Seq ID NOs: 2 to 4 and 6 to 8.

TABLE 2

The ectodomain sequence of recombinant neuraminidases

| SEQ ID NO. | Mutation site(s) | abbreviation |
|---|---|---|
| 2 | I149V | MutA |
| 3 | N344Y | MutB |
| 4 | I365T/S368N | MutC |
| 6 | N344H | MutD |
| 7 | I365E/S366D | MutE |
| 8 | I365T/S366A | MutF |

One of main purposes of the present invention is directed to provide an influenza virus vaccine that may incur cross-protective heterosubtypic immunity. The influenza virus vaccine of the present invention may be an inactivated vaccine, an attenuated influenza, a virus-like particle vaccine or a subunit vaccine, i.e. recombinant NA and expressing vectors, virus-like particles and recombinant influenza virus encoding recombinant NA may be used in vaccine preparation.

In one specific embodiment, the vaccine of the present invention may be delivered to a subject to incur cross-protective immunity against influenza subtypes including emerging human influenza, human seasonal influenza and avian influenza. The pharmacologically active compounds of the present invention may be processed according to conventional pharmaceutical method for preparing pharmaceutical reagents used for delivering to a patient e.g., a mammal (including humans). In another specific embodiment, the delivery may be achieved by approaches for example, but not limited to, subcutaneous, intramuscular, oral administered, spraying or gene gun injection.

The detailed explanation of the present invention is described as follows. The described preferred embodiments are presented for purposes of illustrations and description, and they are not intended to limit the scope of the present invention.

Materials and Methods

Recombinant NA Protein Expression and Purification cDNA from the NA genes of A/Vietnam/1203/2004 (H5N1) (GI: 145284408) and A/Texas/05/2009 (pH1N1) (GI: 255602223) was separately synthesized with insect cell-optimized codon sequences from Genomics, Inc. The coding sequences of the NA H5N1 and pH1N1 ectodomains with additional N-terminal sequences containing gp67 signal peptides, six-His residues, tetrameric human vasodilator-stimulated phosphoprotein (hvsp) domains, and a thrombin cleavage site were cloned into pFastBac expression vectors. Next, rNA proteins were produced using a Bac-to-Bac insect cell expression system (Invitrogen) according to manufacturer instructions. Briefly, Sf9 cells were infected with recombinant baculoviruses expressing the NA ectodomains of H5N1 and pH1N1 for 48 h prior to collecting supernatants for additional rNA protein purification using nickel-chelated resin affinity chromatography (Tosoh). H5N1-rNA and pH1N1-rNA purity was confirmed by Coomassie blue staining. Anti-His HRP-conjugated antibodies (Affymetrix) were used for Western blotting characterization.

Production and Purification of H5N1 and H7N9 VLPs

H5N1 and H7N9 VLPs were produced using the procedures described previously. Briefly, the H5HA gene of A/Thailand/1(KAN-1)/2004 (H5N1), the H7HA gene of A/Shanghai/2/2013 (H7N9), and the M1 gene of A/WSN/1933 (H1N1) were cloned into separate pFastBacDual vectors (Invitrogen). The NINA gene of A/Vietnam/1203/2004 (H5N1), the N9NA gene of A/Shanghai/2/2013 (H7N9), and the M2 gene of A/WSN/1933 (H1N1) were cloned into separate vectors. For H5N1 VLP production, Sf9 cells were co-infected with Bac-H5HA-M1 and Bac-N1NA-M2 recombinant baculoviruses at MOIs of 3 and 1, respectively. Culture supernatants were harvested and concentrated 72 h post-infection. VLPs were further purified using a 20% sucrose solution and centrifugation at 33,000 rpm for 3 h. H5N1 VLPs were obtained and stored at 4° C. until used for NI assays. For H7N9 VLPs, Sf9 cells were co-infected with Bac-H7HA-M1 and Bac-N9NA-M2 recombinant baculoviruses at MOIs of 3 and 1, respectively, for 72 h. Subsequent steps were the same as for H5N1 VLP production.

Mouse Immunizations

BALB/c mice (6-8 weeks old) purchased from the Taiwan National Laboratory Animal Center were immunized twice intramuscularly with 2 or 20 μg of rNA proteins plus 10 μg CpG and 10% PEGb-PLACL, squalene and Span® 85 (PELC) emulsion over a three-week interval as described in a previous report. Sera samples were collected 2 weeks following the second inoculation; splenocytes were harvested and isolated one week later.

Viral Challenges

For the two-dose immunization strategy, BALB/c mice (6-8 weeks old) were placed in one of 5 groups, with each group consisting of 5 mice immunized with either 2 or 20 μg of H5N1-rNA or pH1N1-rNA proteins plus CpG/PELC or PBS over a three-week interval. Three weeks following the second inoculations, all mice were intranasally challenged with 10 $MLD_{50}$ of the H5N1 (NIBRG-14, RG-14), pH1N1 (A/California/07/2009, CA/09), or H7N9 (A/Taiwan/01/2013, TW/13) viruses. PBS-immunized mice were used as a mock control. Survival rates and body weights were recorded daily for 14 days. According to IACUC guidelines, a weight loss of 25% or more was established as an end-point.

Enzyme-Linked Immunosorbant Assays (ELISAs)

Individual wells in 96-well plates were coated with purified rNA proteins (100 μl at 2 μg/ml) and held overnight at 4° C., washed 3 times with PBST (0.05% Tween-20 in PBS), and blocked with blocking buffer (1% BSA in PBS) for at least 1 h. Next, 100 μl of two-fold serially diluted sera samples were added and held at RT for 1 h, followed by 3 additional washes with PBST. HRP-conjugated goat anti-mouse IgG antibodies (Bethyl Laboratories, Inc.) were added to each well, incubated for 1 h, and washed 3 times with PBST. Anti-NA IgG titers were determined by adding TMB substrate (Biolegend), holding for 15 min at RT, and stopping reactions with 2N $H_2SO_4$. End-point titers were determined as the reciprocal of most diluted sera concentrations giving a mean optical density (OD) of 450 nm above 0.2.

Neuraminidase-Inhibiting (NI) Assays

NA-inhibiting (NI) antibodies were measured using a previously described fetuin-based assay procedure. Briefly, 96-well plates were coated with 50 μg/mL fetuin (Sigma) and held overnight at 4° C. before being washed 3 times with PBST and blocked with blocking buffer for 2 h. Two-fold serially diluted sera samples in blocking buffer were incubated with equal volumes of 1 μg VLPs (H5N1 or H7N9) or $10^5$ p.f.u. viruses (pH1N1 or H3N2) for 1 h at 37° C., added to the fetuin-coated plates and held for another 1 h at 37° C., and then washed 3 times with PBST. Peroxidase-labeled peanut agglutinin (100 μl at 2.5 μg/mL) (Sigma) was added to each well, incubated for 1 h at RT, and washed 3 times with PBST. The NA activity levels of viruses (pH1N1 or H3N2) and VLPs (H5N1 or H7N9) were determined by adding TMB substrate (Biolegend), holding for 15 min at RT, and stopping reactions with 2N $H_2SO_4$. Plates were read with an ELISA reader (Tecan) at an OD of 450 nm. Corresponding IC50 values were defined as the reciprocal serum dilution inhibiting 50% of viral NA enzyme activity.

NA-Specific Antibody-Secreting B Cells

Splenocytes were collected from each group of rNA-immunized or PBS-immunized mice 3 weeks following the second inoculations. Multiscreen 96-well filtration plates (Millipore) were coated with rNA proteins (1 μg per well) and incubated overnight at 4° C. Plates were blocked with 200 μl/well of complete RPMI-1640 (10% FBS, 1×P/S, 1× sodium pyruvate, 1×NEAA and 100 μM β-ME) and held for 1 h at RT. Splenocytes ($2\times10^5$) diluted in complete RPMI-1640 were added to individual plates and incubated for 48 h at 37° C. After 3 washes with PBST, HRP-conjugated anti-mouse IgG antibodies were added to each well and held for 2 h at RT. After 3 PBST and 2 PBS washes, AEC substrate was added to each plate and held at RT for 10~60 min before stopping reactions with $ddH_2O$. Immunospots for each immunized group were determined using an ELISPOT Plate Reader (CTL, Inc.).

Production of Chimeric pH1N1/PR8 Influenza Viruses

A mixture of 293T ($3.5\times10^5$) and MDCK cells ($5\times10^5$) were seeded into 2 mL OPTI-MEM media at each well of 6-well plates and incubated overnight in a $CO_2$ incubator. The present invention used the eight distinct component plasmids of influenza virus to produce the chimeric pH1N1/PR8 viruses, inclusive of the WT HA from A/Texas/05/2009 (pH1N1) or PR8 strain, the WT or mutant (I365T&S366N) NA components from the A/Texas/05/2009 viral strain and other six components all from the PR8 viral strain. These eight DNA plasmids were simultaneously co-transfected into 293T/MDCK cell mixtures using a TransIT-LT1 transfection reagent (Mirus Bio LLC). TransIT-LT1 reagent/DNA complex mixtures were incubated overnight at 37° C. Medium was replaced with 3 mL fresh OPTI-MEM containing 0.5 μg/mL TPCK-trypsin and incubated for another 2~3 days. Supernatants were collected, titrated, and held at −80° C. until used in the experiments.

Plaque Assays for Chimeric pH1N1/PR8 Influenza Viruses

MDCK cells ($6\times10^5$/well) were held overnight at 37° C. Monolayer MDCK cells were infected with serially diluted PR8, PR8 x Texas HA (THA) x Texas NA (TNA) or PR8 x THA x TNA (I365T/S366N) RG viruses for 1 h at 37° C. Supernatants were removed and washed twice with PBS. Infected MDCK cells were overlaid with MEM-α plus 0.5% agarose. After another 48 hours of incubation at 37° C., infected cells were fixed with 4% paraformaldehyde and stained with 1% crystal violet solution. Plaque numbers were observed and calculated.

Statistical Analysis

All results were analyzed using Student's t tests. Asterisks in each Fig. indicate statistical significance (*, $p<0.05$; , $p<0.01$; *, $p<0.001$).

Figure 1B:
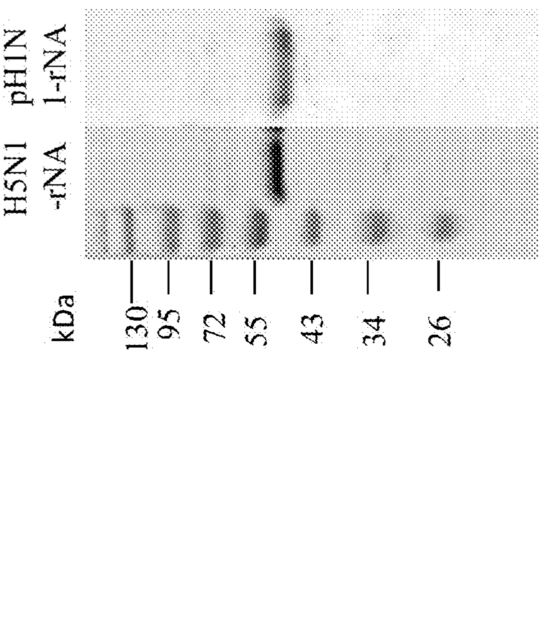
Figure 1C:
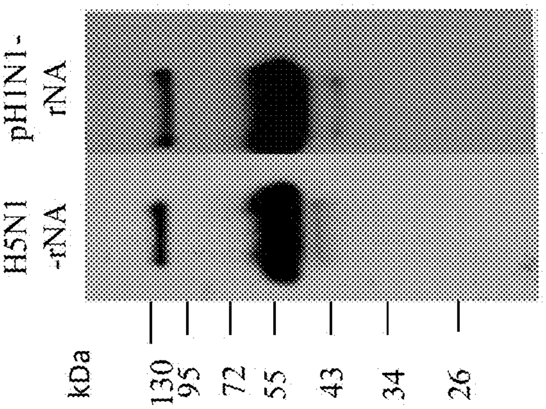
Figure 1D:
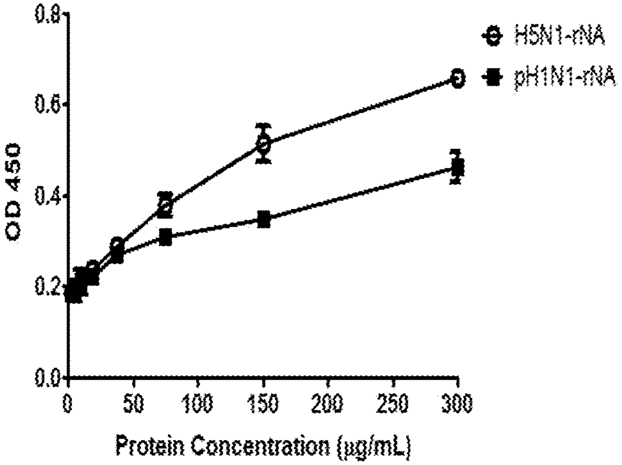
Figures 3A, 3B, 3C, 3D, 3E, 3F, 3G, 3H:
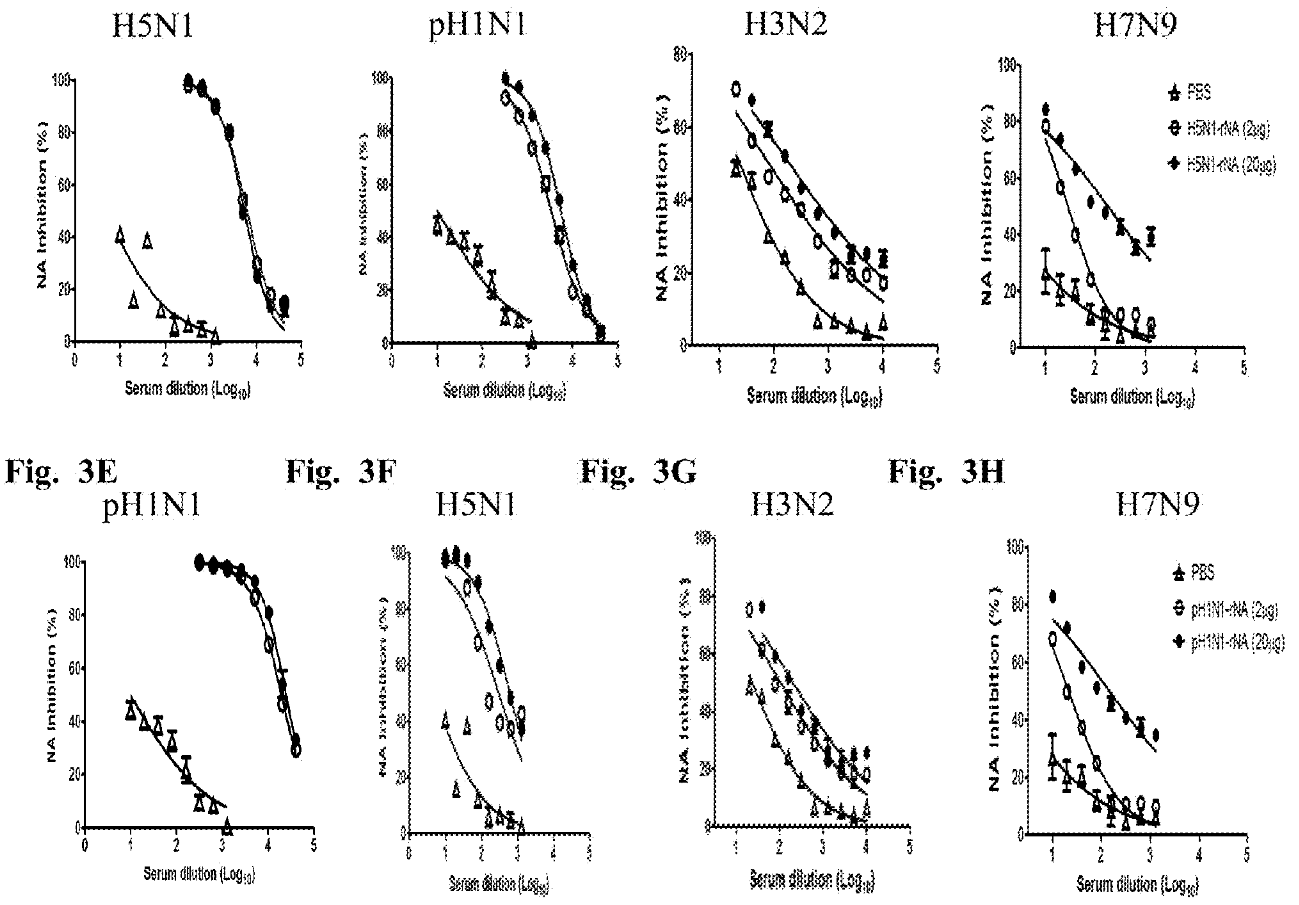
FIGS. 3A to 3H illustrate NA-inhibiting antibodies elicited by H5N1-rNA and pH1N1-rNA immunization against H5N1, pH1N1, H3N2 and H7N9 virus.

H5N1-rNA and pH1N1-rNA Proteins Expressed and Purified Using a Baculovirus-Insect Cell Expression System The construction diagram of soluble H5N1-rNA and pH1N1-rNA proteins presented as FIG. 1A was produced from the culture supernatants of Sf9 cells infected by recombinant baculoviruses and purified using Ni-chelated affinity chromatography. Soluble H5N1-rNA and pH1NA-rNA yields were approximately 0.5 mg/L and 0.25 mg/L, respectively, with 80-90% purity (FIG. 1B). According to results from SDS-PAGE gels with Coomassie blue staining (FIG. 1B) and Western blotting (FIG. 1C), purified H5N1-rNA and pH1N1-rNA proteins had molecular weights of 53 kDa each. Based on Eadie-Hofstee measurements, H5N1-rNA and pH1N1-rNA Km values were 2.80 and 1.90, respectively (FIG. 1D), indicating enzyme activity in insect cell-expressed H5N1-rNA and pH1N1-rNA.

NA-Specific IgG Antibodies were Induced by H5N1-rNA and pH1N1-rNA Immunizations

Groups of five female BALB/c mice were i.m. immunized with two doses of H5N1-rNA or pH1N1-rNA proteins (2 or 20 μg per dose) over a three-week interval. Antisera were collected 2 weeks following the second immunizations. Data for NA-specific IgG titers against the same immunogens (H5N1-rNAs or pH1N1-rNA proteins) in each group are presented in FIG. 2A. The present invention used an anti-mouse N1NA-specific antibody as a positive control and PBS-immunized sera as a negative control ($10^{3.5-4}$ and undetectable NA-specific IgG titers, respectively). As shown in FIG. 2A, mice immunized with 20 μg of H5N1-rNA or pH1N1-rNA exhibited slightly higher NA-specific total IgG titers compared to mice immunized with 2 μg of H5N1-rNA or pH1N1-rNA. The present invention also performed ELISA assays with H5N1 VLPs (FIG. 2B) and the pH1N1 (A/California/04/2009) virus (FIG. 2C). Our data indicate that at either 2 or 20 μg, both H5N1-rNA and pH1N1-rNA cross-reacted with H5N1 VLPs and the pH1N1 virus to induce similar amounts of total IgG titers (FIG. 2B-2C). Similar cross-reactive results were also found for the H3N2 virus (A/Udorn/307/1972) and H7N9 VLPs (FIGS. 2D-2E). No significant differences were noted for either IgG1 or IgG2a subclass titers in the same immunization groups. The single exception was significantly greater IgG2a for mice immunized with 20 μg H5N1-rNA (data not shown).

NI Antibodies are Elicited by H5N1-rNA and pH1N1-rNA Immunizations

Figure 4:
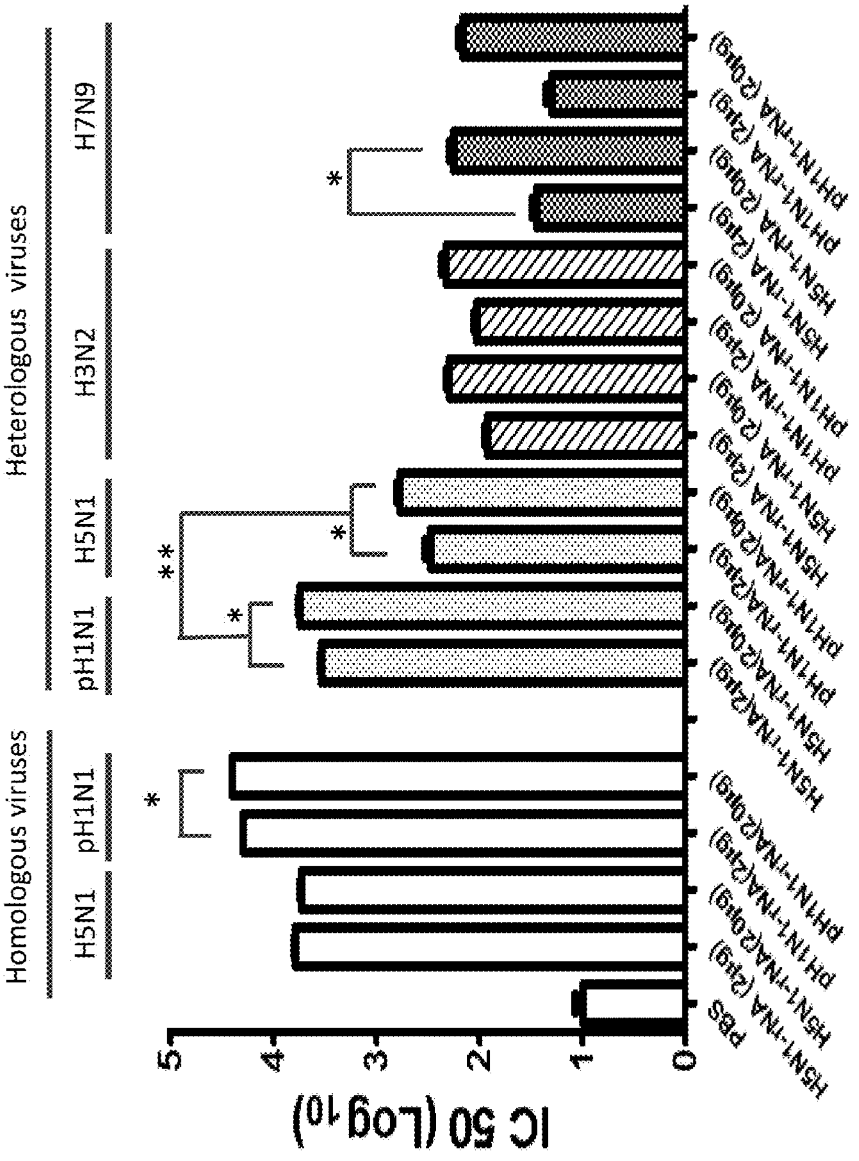
FIG. 4 illustrates the corresponding IC50 values elicited by H5N1-rNA and pH1N1-rNA immunization against homologous and heterologous viruses.

To measure NI antibody titers, two-fold serially diluted serum samples from each immunization group were mixed with 1 μg of H5N1-VLP, $10^5$ p.f.u. of the pH1N1 (A/California/04/2009) virus, $10^5$ p.f.u. of the H3N2 (A/Udorn/307/1972) virus, or 1 μg of H7N9-VLP, and then examined using fetuin-based assays. NA-inhibiting percentages and NI titers against the same group two viruses, H5N1 and pH1N1, in each immunization group are shown in FIGS. 3A-3B and 3E-3F. Those results indicate dose-dependency, with NI curves from all rNA immunization groups significantly higher than the curves for the PBS immunization group. NA-inhibiting percentages and NI titers were also demonstrated in the H3N2 virus and H7N9 VLPs, with similar results but lower NI titers (FIGS. 3C-3D and 3G-3H). Regarding IC50 values, similar NI titer ranges were observed against the homologous viruses: 3.7-3.8 for H5N1-rNA immunization against H5N1 and 4.3-4.4 for pH1N1-rNA immunization against pH1N1 (FIG. 4). However, significant differences were noted among the six immunization groups in terms of NI titers against the H5N1, pH1N1, H3N2 and H7N9 heterologous viruses. Both H5N1-rNA immunization groups (2 and 20 μg) expressed higher heterosubtypic NI titers against pH1N1 compared to titers elicited by the two pH1N1-rNA immunization groups against H5N1 viruses. In contrast, H5N1-rNA and pH1N1-rNA elicited lower NI titers, with IC50 values less than 2.32 for all groups immunized against the H3N2 and H7N9 viruses (FIG. 31). Our data indicate that the effect of H5N1-rNA immunization was limited to more potent heterosubtypic NI antibodies against pH1N1 viruses.

Antibody-Secreting B Cells Detected in Splenocytes

Figure 5:
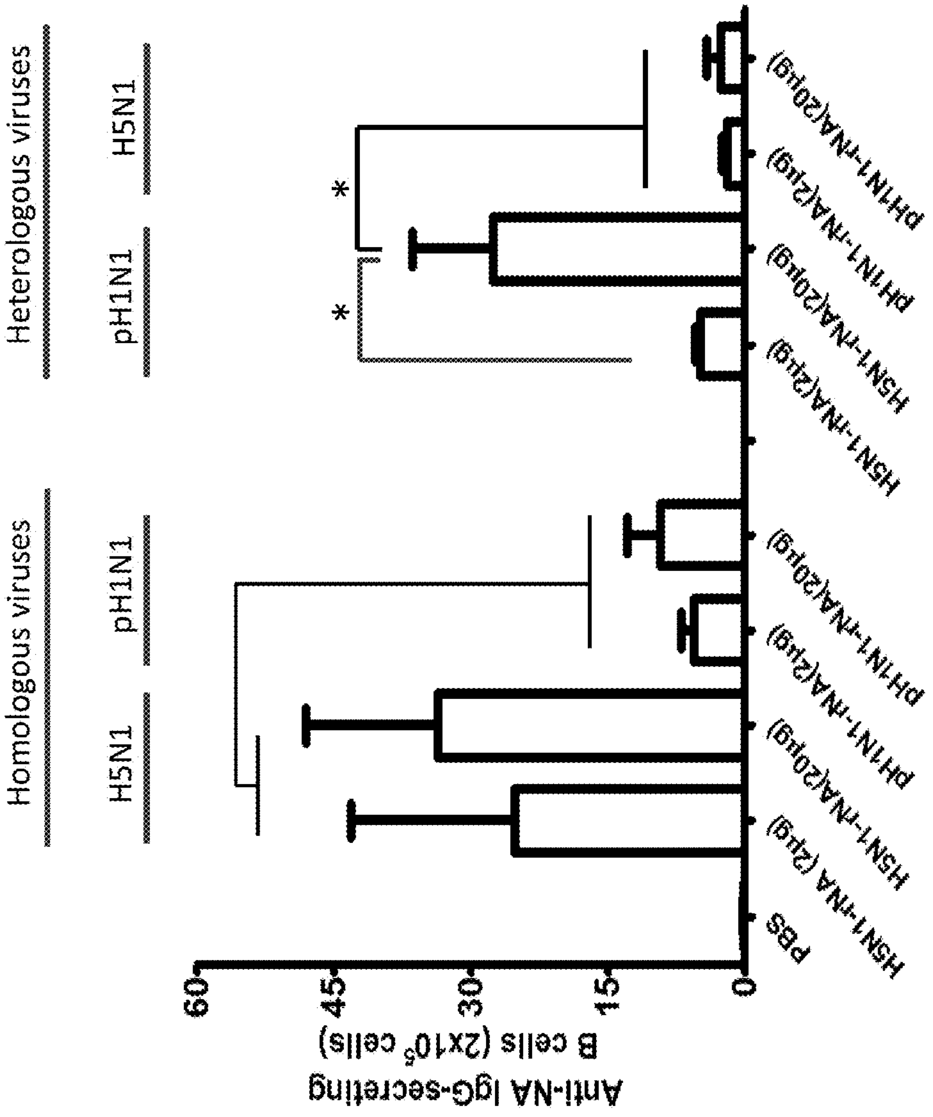
FIG. 5 illustrates detection of H5N1-rNA and pH1N1-rNA specific antibodies secreting B-cells in spleens.

To measure anti-NA IgG-secreting B cells elicited by H5N1-rNA or pH1N1-rNA, splenocytes were collected from immunized mice 3 weeks after their second immunizations, reacted with 1 μg H5N1-rNA or pH1N1-rNA protein per well, and examined using ELISPOT assays. The results shown in FIG. 5 indicate that the numbers of spots against homologous viruses due to H5N1-rNA immunization were slightly higher than those resulting from pH1N1-rNA immunization. Significantly higher numbers of spots against H5N1 and pH1N1 heterologous viruses were only noted in the 20 μg H5N1-rNA immunization group, which also exhibited higher quantities of ASCs in splenocytes against homologous and heterologous H5N1 and pH1N1 viruses.

Protective Immunity Against H5N1, pH1N1 and H7N9 Virus Challenges

Figures 6A, 6B, 6C, 6D, 6E:
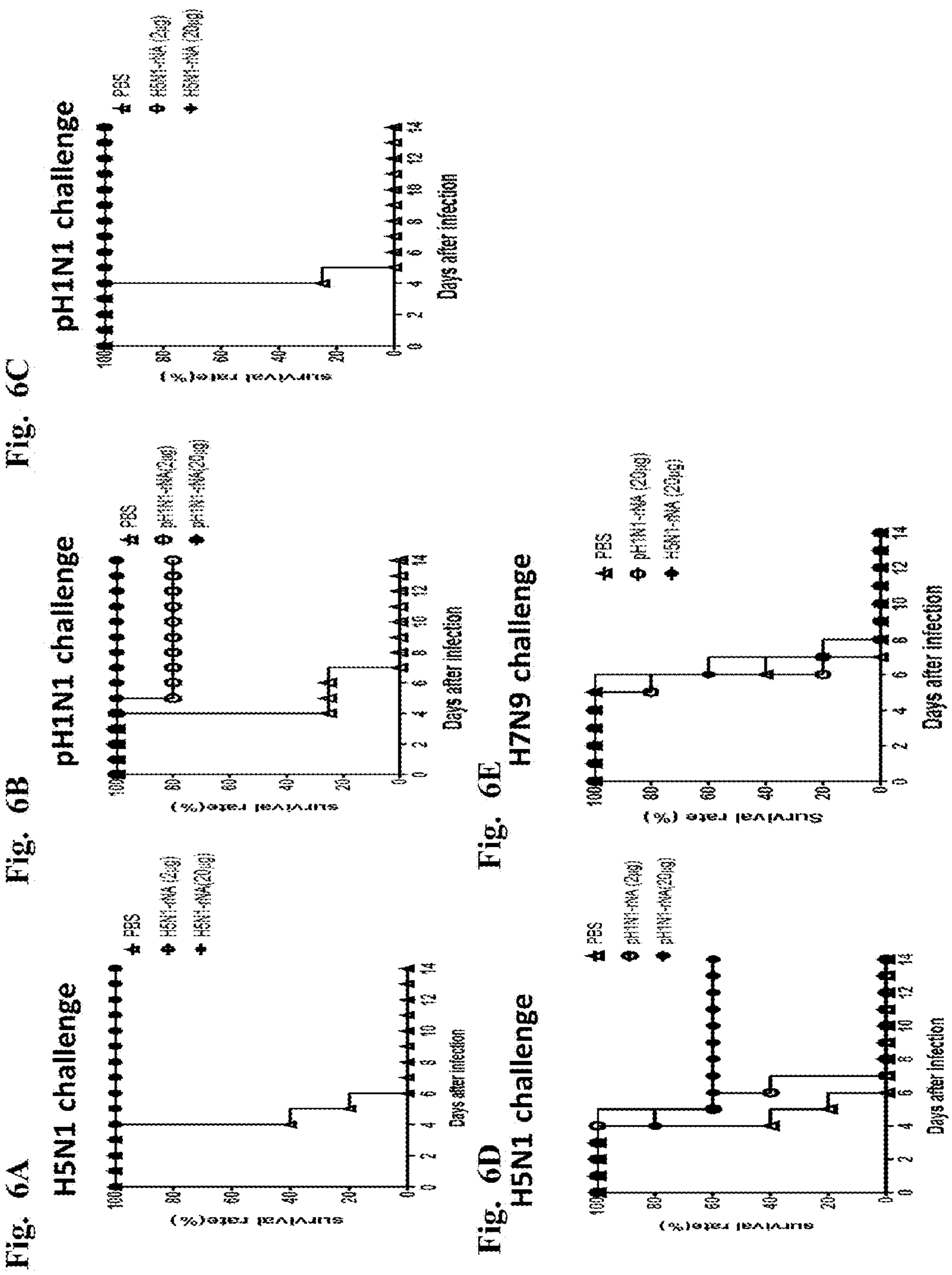
FIGS. 6A to 6E illustrate H5N1-rNA and pH1N1-rNA protective immune responses against different virus challenges.
Figure 7A:
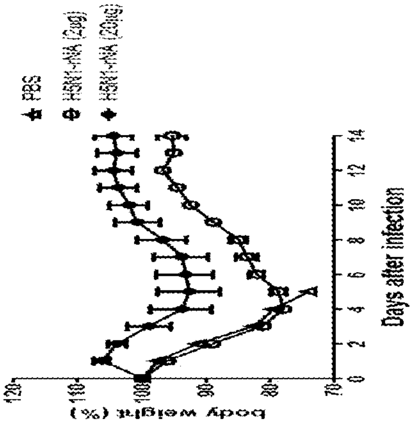
FIGS. 7A to 7E illustrate body weight recovery tied to H5N1-rNA and pH1N1-rNA immunization responses against different virus challenges.
Figure 7B:
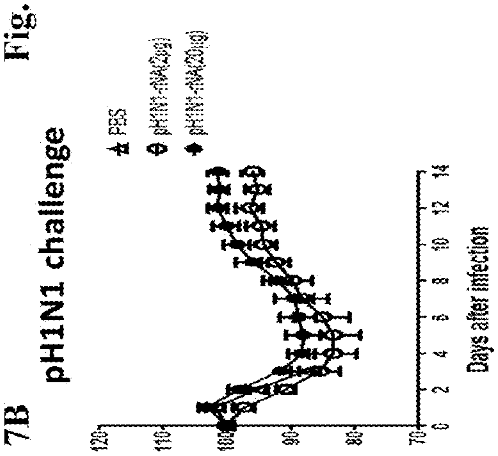
Figure 7C:
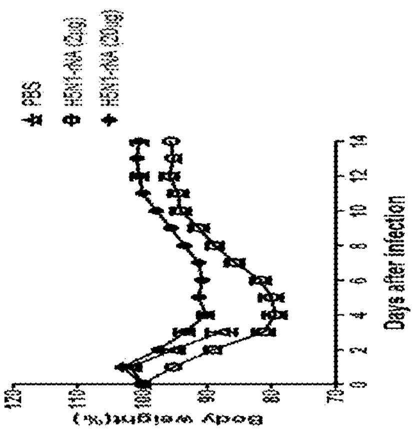
Figure 7D:
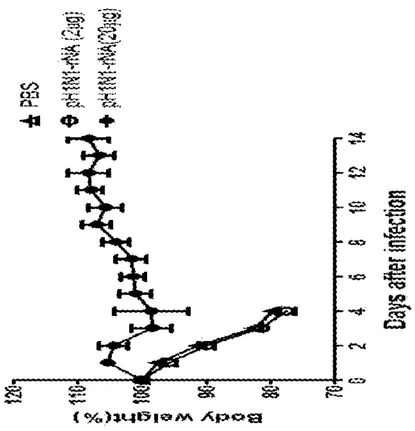
Figure 7E:
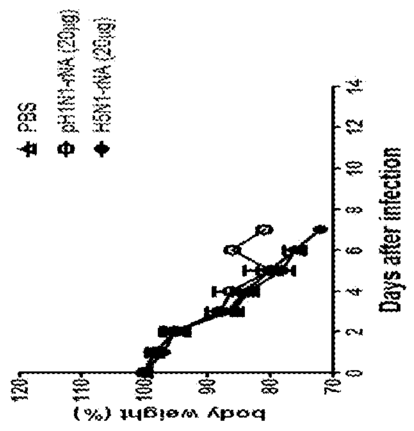
Figure 9:
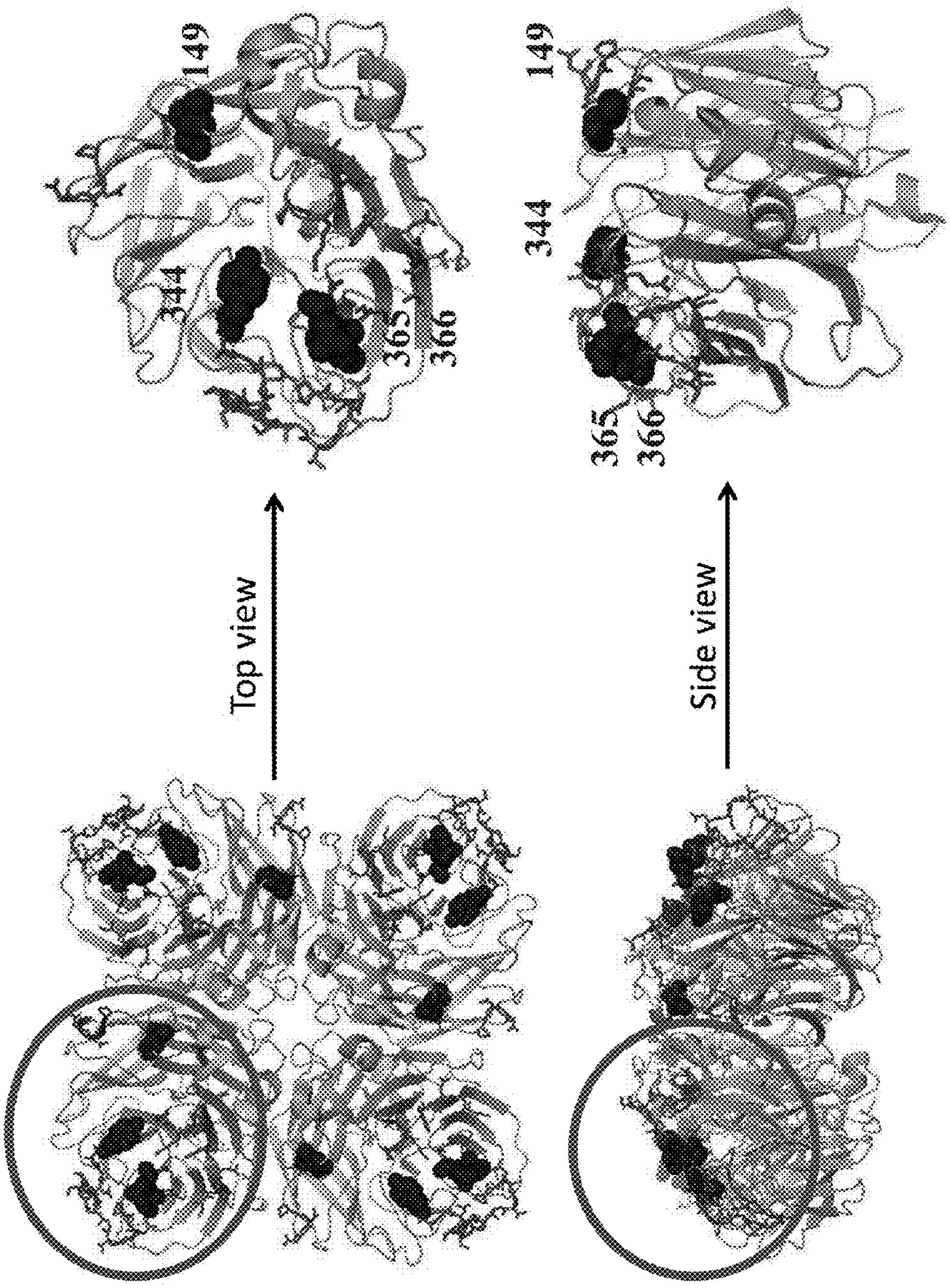
FIG. 9 illustrates the top view and side view of pH1N1 NA.

To assess protective immunity triggered by rNA immunizations, mice immunized with 2 or 20 μg of H5N1-rNA or pH1N1-rNA proteins were challenged with 10 $MLD_{50}$ of H5N1 (RG-14), pH1N1 (CA/09) or H7N9 (TW/13) viruses 3 weeks following their second immunizations. According to the results shown in FIGS. 6A-6B with the exceptions of an 80% survival rate for mice immunized with 2 μg of pH1N1-rNA and a 0% rate for the PBS control mice, all immunization groups had 100% survival rates against homologous H5N1 or pH1N1 viral challenges. Significantly lower body weight losses were observed for mice in the 20 μg H5N1-rNA and 20 μg pH1N1-rNA immunization groups challenged with homologous H5N1 or pH1N1 compared to those in the 2 μg H5N1-rNA and 2 μg pH1N1-rNA immunization groups (FIGS. 7A-7B). In terms of cross-protection levels, mice receiving either 2 or 20 μg H5N1-rNA inoculations exhibited complete protection against pH1N1 viral challenges (FIG. 6C), with significantly lower body weight losses noted in the 20 μg group (FIG. 7C). A 60% survival rate (FIG. 6D) and faster weight loss recovery following challenges with the heterologous H5N1 virus were observed in the 20 μg pH1N1-rNA immunization group (FIG. 7D). Zero protection against a H7N9 virus challenge was observed in the 20 μg H5N1-rNA and 20 μg pH1N1-rNA immunization groups (FIGS. 6E and 7E).

Cross-Reactive NI Antibodies Elicited by pH1N1-rNA Mutant Proteins

Figures 10A, 10B, 10C, 10D:
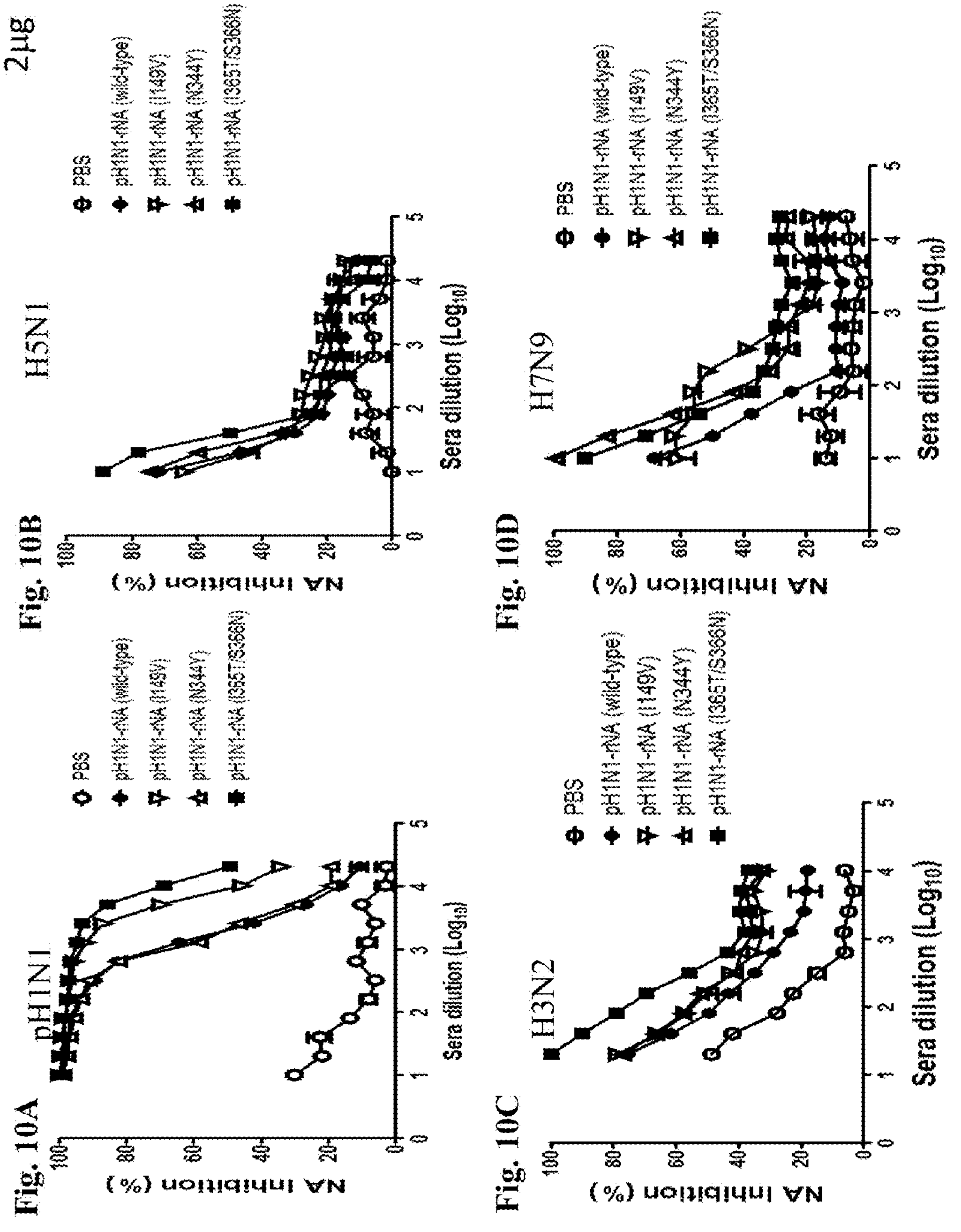
FIGS. 10A to 10D illustrate the increased NA-inhibiting antibody curves produced by WT and group 1 mutant pH1N1-rNAs immunizations against different virus strains.
Figure 11:
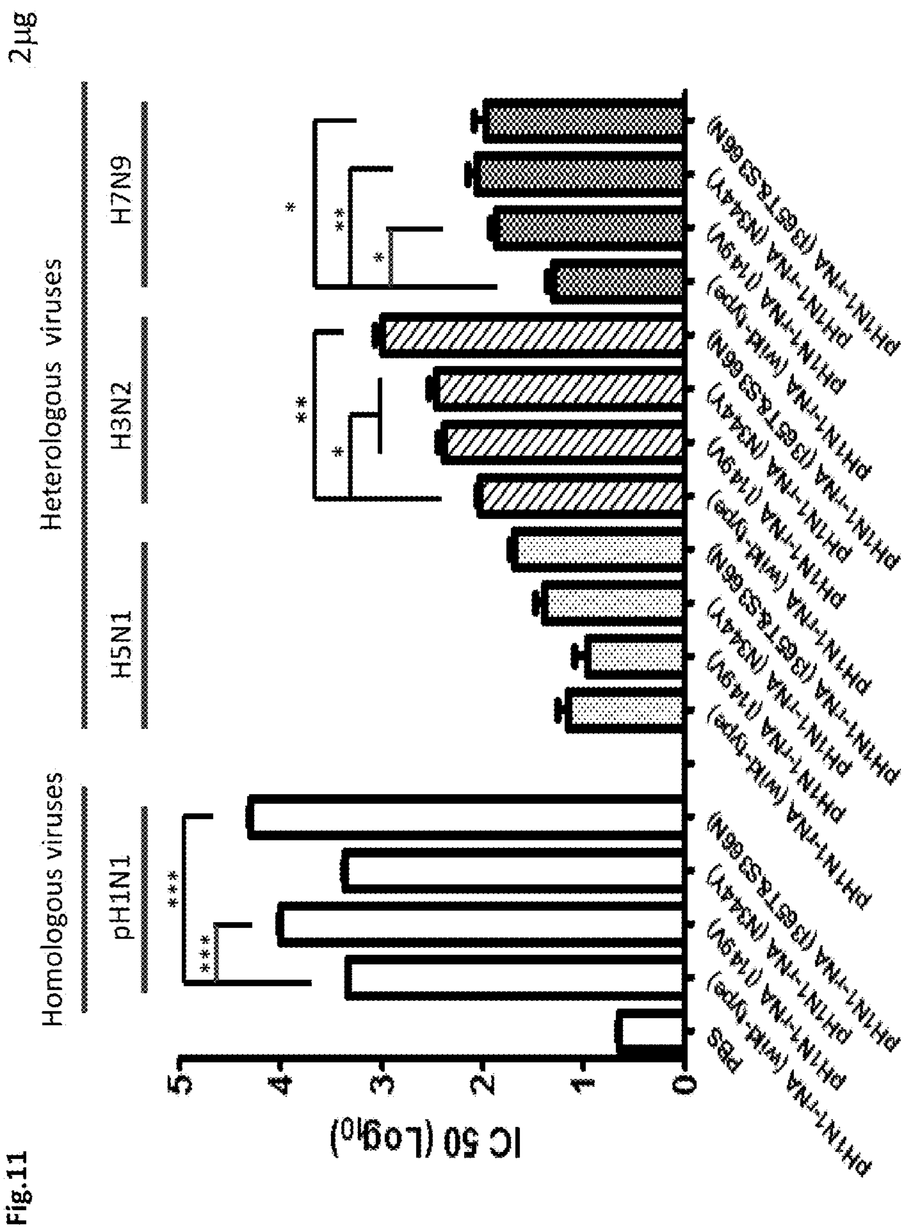
FIG. 11 illustrates the corresponding IC50 values against the homologous pH1N1 viruses and the heterosubtypic H5N1, H3N2 and H7N9 viruses.
Figures 13A, 13B, 13C, 13D:
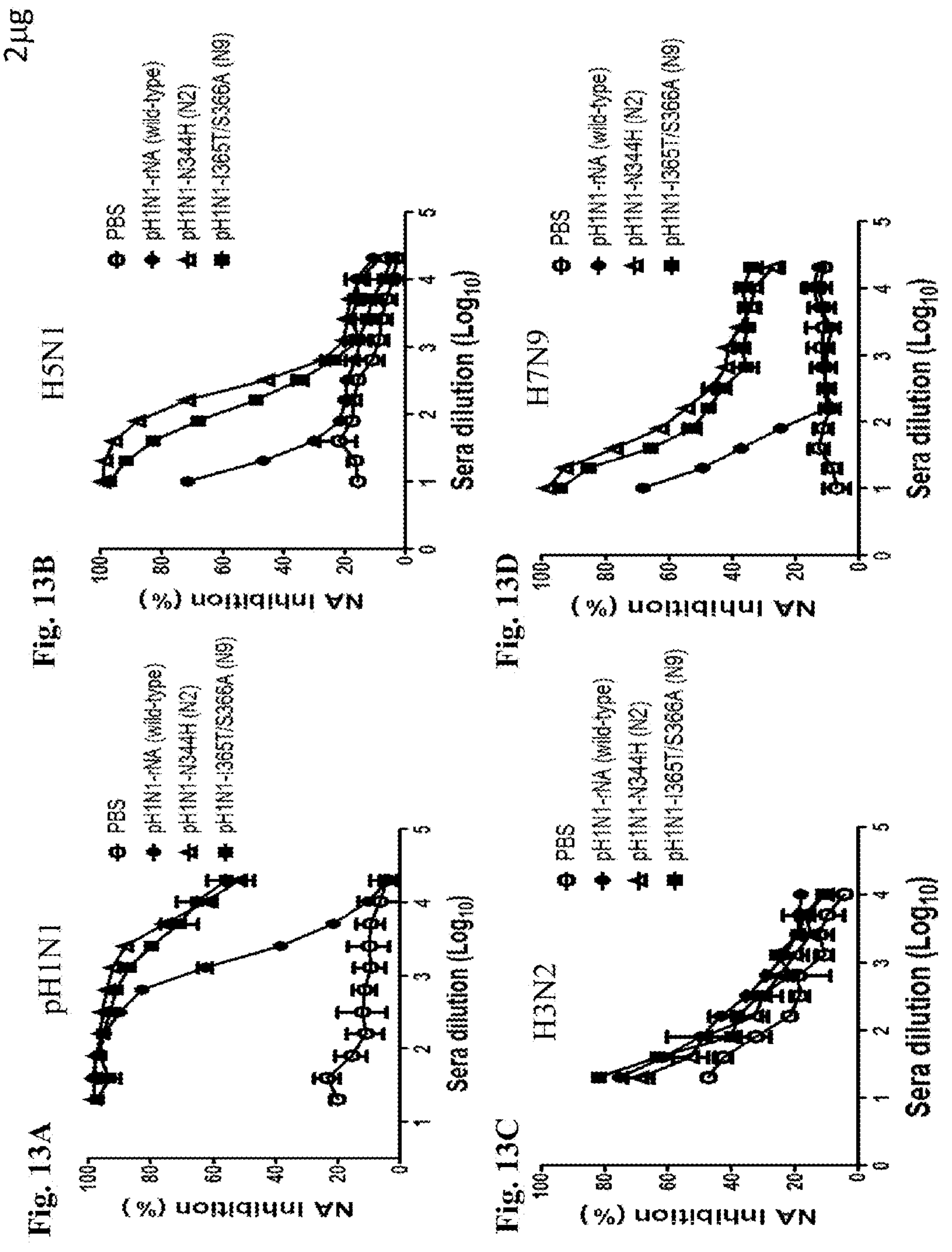
FIGS. 13A to 13D illustrate increased NA-inhibiting antibody curves produced by WT and group2 mutant pH1N1-rNAs immunizations against different virus strains.

To add detail to our investigation of cross-reactive NI epitopes, the present invention aligned the amino acid sequences of A/Vietnam/1203/2004 (H5N1), A/Texas/05/2009 (pH1N1), A/Udorn/307/1972 (H3N2) and A/Shanghai/02/2013 (H7N9). As shown in FIG. 8, the present invention identified 34 different amino acids (in red) in the NA ectodomains of the two sequences (94.6% identical). Previous reports have identified influenza NA enzyme catalytic sites at residues 118-119, 151-152, 198, 224, 227, 243, 274, 276-277, 292, 330, 350 or 425, therefore the present invention targeted residues 149, 344, 365 and 366—all located close to NA enzyme-active sites and contributing to NI antibody elicitation. Site-directed mutagenesis at these four residues produced three mutant pH1N1-rNA proteins: I149V, N344Y and I365T/S366N (not illustrated). Results from an analysis of anti-sera from the wild type and three mutant pH1N1-rNAs show that the I149V and I365T/S366N mutant proteins elicited more NI antibodies against the homologous pH1N1 strain (FIG. 10A), with the I365T/S366N protein eliciting more potent cross-reactive NI antibodies against the H5N1 (FIG. 10B), H3N2 (FIG. 10C) and H7N9 viruses (FIG. 10D). Corresponding IC50 values calculated from NI response curves indicate that the I149V and I365T/S366N mutant proteins resulted in increased NI titers against the homologous pH1N1 viruses, and that all three mutant proteins resulted in increased NI titers against the heterosubtypic H3N2 and H7N9 viruses (FIG. 11). The I365T/S366N mutation of pH1N1-rNA induced the highest quantities of NI antibody titers against the homologous and heterosubtypic strains. The present invention also constructed and expressed the other mutant pH1N1-rNA proteins changing from pH1N1 to H3N2 or H7N9, as FIG. 12 described. Results from an analysis of anti-sera from the wild type and three mutant pH1N1-rNAs show that the pH1N1-N344H (N2) and pH1N1-I365T/S366A (N9) mutant proteins elicited more NI antibodies against the homologous pH1N1 strain (FIG. 13A) and heterologous H7N9 strain (FIG. 13D), with similar cross-reactive NI antibodies against the H5N1 (FIG. 13B) and H3N2 (FIG. 13C) viruses. Corresponding IC50 values calculated from NI response curves indicate that the pH1N1-N344H (N2) and pH1N1-I365T/S366A (N9) mutant proteins resulted in increased NI titers against the homologous pH1N1 viruses, and that pH1N1-

Figure 14:
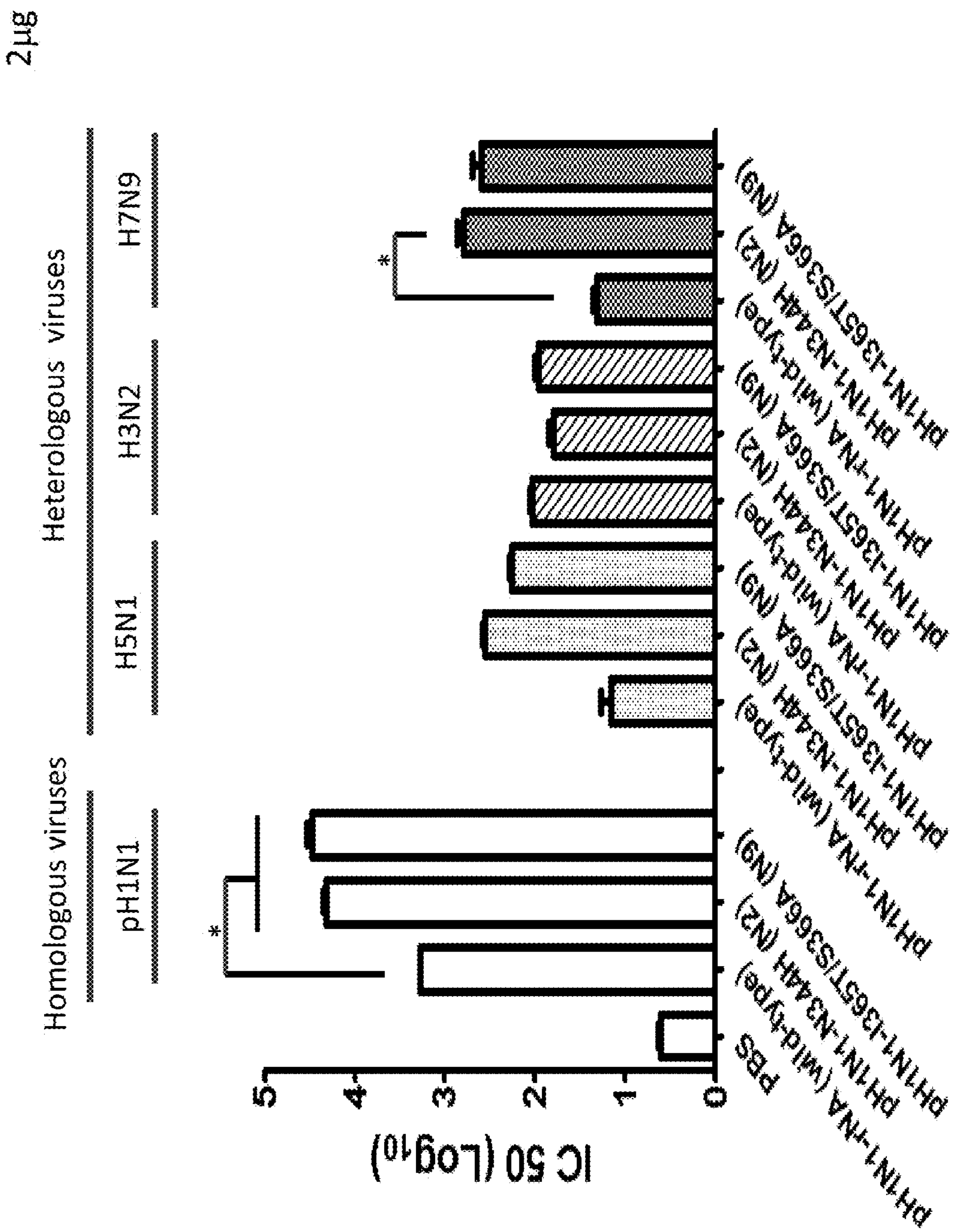
FIG. 14 illustrates the corresponding IC50 values against the homologous pH1N1 viruses and the heterosubtypic H5N1, H3N2 and H7N9 viruses.

N344H (N2) mutant protein resulted in increased NI titers against the heterosubtypic H7N9 viruses (FIG. 14).

Construction of the I365T/S366N Mutant of Chimeric pH1N1/PR8 Viruses

The present invention used a PR8 (A/Puerto Rico/8/1934 (H1N1))-based reverse genetic system with replacement HA and NA genes of A/Texas/05/2009 (pH1N1) to construct chimeric pH1N1/PR8 viruses of the wild type NA gene (PR8 x THA x TNA), and a I365T/S366N mutant of the NA gene (PR8 x THA x TNA-I365T/S366N). The obtained chimeric pH1N1/PR8 viruses with the I365T/S366N mutation had similar plaque morphologies (FIG. 15A) with the titers of $6\times10^6$ PFU/ml in MDCK cells. The present invention also measured the replication kinetics of the three viruses (PR8 RG, PR8 x THA x TNA and PR8 x THA x TNA-I365T/S366N) in MDCK cells at MOIs of 0.01. No significant differences in replication kinetics were observed in the I365Y/S366N mutant viruses (FIG. 15B) or in NA enzymatic activity compared to the PR8 and chimeric pH1N1/PR8 viruses (FIG. 15C).

CONCLUSION

NA-based influenza vaccines are attractive because of the smaller number of changes in NA antigens compared to HA antigens in host immune systems. For this study, the present invention constructed and purified H5N1-rNA and pH1N1-rNA proteins from Sf9 insect cells, and found that mice immunized with H5N1-rNA and pH1N1-rNA proteins exhibited higher quantities of NA-specific total IgG, IgG1, IgG2a subclass and NI antibody titers, increased numbers of ASCs in splenocytes, and better protective immunity against live virus challenges. H5N1-rNA immunization was found to induce more potent cross-reactive NI antibodies and protective immunity against pH1N1 viruses compared to pH1N1-rNA immunization against H5N1 viruses. Cross-reactive NI epitopes were further dissected by immunization of pH1N1-rNA proteins with I149V, N344Y and I365T/S366N NA mutations. The I365T/S366N mutation of pH1N1-rNA was found to increase cross-reactive NI antibodies against the H5N1, H3N2 and H7N9 viruses.

While the invention can be subject to various modifications and alternative forms, a specific example thereof has been shown in the drawings and is herein described in detail. It should be understood, however, that the invention is not to be limited to the particular form disclosed, but on the contrary, the invention is to cover all modifications, equivalents, and alternatives falling within the spirit and scope of the appended claims.

What is claimed is:

1. A recombinant neuraminidase, comprising an ectodomain provided with an amino acid sequence at least 95% identical to SEQ ID NO: 1, wherein the amino acids at positions 365 and 366 are replaced from IS to TN.

2. The recombinant neuraminidase as claimed in claim 1, wherein the amino acid sequence is at least 97% identical to SEQ ID NO: 1.

3. The recombinant neuraminidase as claimed in claim 1, wherein the amino acid sequence is at least 99% identical to SEQ ID NO: 1.

4. The recombinant neuraminidase as claimed in claim 1, wherein the amino acid sequence is selected from Seq ID NO: 4.

5. A recombinant influenza virus, comprising:

a recombinant neuraminidase, comprising an ectodomain provided with an amino acid sequence at least 95% identical to SEQ ID NO: 1, wherein the amino acids at positions 365 and 366 is replaced from IS to TN.

6. The recombinant influenza virus as claimed in claim 5, wherein the amino acid sequence is at least 97% identical to SEQ ID NO: 1.

7. The recombinant influenza virus as claimed in claim 5, wherein the amino acid sequence is at least 99% identical to SEQ ID NO: 1.

8. The recombinant influenza virus as claimed in claim 5, wherein the amino acid sequence is selected from Seq ID NO: 4.

9. An influenza virus vaccine, comprising:

a recombinant neuraminidase, comprising an ectodomain provided with an amino acid sequence at least 95% identical to SEQ ID NO: 1, wherein the amino acids at positions 365 and 366 is replaced from IS to TN.

10. The influenza virus vaccine, as claimed in claim 9, wherein the amino acid sequence is at least 97% identical to SEQ ID NO: 1.

11. The influenza virus vaccine as claimed in claim 9, wherein the amino acid sequence is at least 99% identical to SEQ ID NO: 1.

12. The influenza virus vaccine as claimed in claim 9, wherein the amino acid sequence is selected from Seq ID NO: 4.

13. The influenza virus vaccine as claimed in claim 9, wherein the influenza virus vaccine is an inactivated vaccine, an attenuated influenza, a virus-like particle vaccine or a subunit vaccine.

* * * * *

SEQUENCE LISTING

```
<160> NUMBER OF SEQ ID NOS: 11

<210> SEQ ID NO 1
<211> LENGTH: 469
<212> TYPE: PRT
<213> ORGANISM: Influenza A virus
<220> FEATURE:
<223> OTHER INFORMATION: A/Texas/05/2009

<400> SEQUENCE: 1

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190
```

-continued

```
Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 2
<211> LENGTH: 469
<212> TYPE: PRT
<213> ORGANISM: Influenza A virus
<220> FEATURE:
<223> OTHER INFORMATION: Mut A

<400> SEQUENCE: 2

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80
```

-continued

```
Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465
```

-continued

<210> SEQ ID NO 3
<211> LENGTH: 469
<212> TYPE: PRT
<213> ORGANISM: Influenza A virus
<220> FEATURE:
<223> OTHER INFORMATION: Mut B

<400> SEQUENCE: 3

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Tyr Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365
```

-continued

```
Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 4
<211> LENGTH: 469
<212> TYPE: PRT
<213> ORGANISM: Influenza A virus
<220> FEATURE:
<223> OTHER INFORMATION: Mut C

<400> SEQUENCE: 4

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255
```

```
Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Thr Asn Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 5
<211> LENGTH: 485
<212> TYPE: PRT
<213> ORGANISM: Influenza A virus
<220> FEATURE:
<223> OTHER INFORMATION: Mut A+ Mut B+ Mut C

<400> SEQUENCE: 5

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
            20                  25                  30

Ala His Ser Ala Phe Ala His His His His His His Ser Ser Ser Asp
        35                  40                  45

Tyr Ser Asp Leu Gln Arg Val Lys Gln Glu Leu Leu Glu Glu Val Lys
    50                  55                  60

Lys Glu Leu Gln Lys Val Lys Glu Glu Ile Ile Glu Ala Phe Val Gln
65                  70                  75                  80

Glu Leu Arg Lys Arg Gly Ser Leu Val Pro Arg Gly Ser Pro Ser Arg
                85                  90                  95

Ser Val Val Ser Val Lys Leu Ala Gly Asn Ser Ser Leu Cys Pro Val
            100                 105                 110

Ser Gly Trp Ala Ile Tyr Ser Lys Asp Asn Ser Val Arg Ile Gly Ser
        115                 120                 125
```

-continued

```
Lys Gly Asp Val Phe Val Ile Arg Glu Pro Phe Ile Ser Cys Ser Pro
    130                 135                 140

Leu Glu Cys Arg Thr Phe Phe Leu Thr Gln Gly Ala Leu Leu Asn Asp
145                 150                 155                 160

Lys His Ser Asn Gly Thr Val Lys Asp Arg Ser Pro Tyr Arg Thr Leu
                165                 170                 175

Met Ser Cys Pro Ile Gly Glu Val Pro Ser Pro Tyr Asn Ser Arg Phe
            180                 185                 190

Glu Ser Val Ala Trp Ser Ala Ser Ala Cys His Asp Gly Ile Asn Trp
        195                 200                 205

Leu Thr Ile Gly Ile Ser Gly Pro Asp Asn Gly Ala Val Ala Val Leu
    210                 215                 220

Lys Tyr Asn Gly Ile Ile Thr Asp Thr Ile Lys Ser Trp Arg Asn Asn
225                 230                 235                 240

Ile Leu Arg Thr Gln Glu Ser Glu Cys Ala Cys Val Asn Gly Ser Cys
                245                 250                 255

Phe Thr Val Met Thr Asp Gly Pro Ser Asn Gly Gln Ala Ser Tyr Lys
            260                 265                 270

Ile Phe Arg Ile Glu Lys Gly Lys Ile Val Lys Ser Val Glu Met Asn
        275                 280                 285

Ala Pro Asn Tyr His Tyr Glu Glu Cys Ser Cys Tyr Pro Asp Ser Ser
    290                 295                 300

Glu Ile Thr Cys Val Cys Arg Asp Asn Trp His Gly Ser Asn Arg Pro
305                 310                 315                 320

Trp Val Ser Phe Asn Gln Asn Leu Glu Tyr Gln Ile Gly Tyr Ile Cys
                325                 330                 335

Ser Gly Ile Phe Gly Asp Asn Pro Arg Pro Asn Asp Lys Thr Gly Ser
            340                 345                 350

Cys Gly Pro Val Ser Ser Asn Gly Ala Tyr Gly Val Lys Gly Phe Ser
        355                 360                 365

Phe Lys Tyr Gly Asn Gly Val Trp Ile Gly Arg Thr Lys Ser Thr Asn
    370                 375                 380

Ser Arg Asn Gly Phe Glu Met Ile Trp Asp Pro Asn Gly Trp Thr Gly
385                 390                 395                 400

Thr Asp Asn Asn Phe Ser Ile Lys Gln Asp Ile Val Gly Ile Asn Glu
                405                 410                 415

Trp Ser Gly Tyr Ser Gly Ser Phe Val Gln His Pro Glu Leu Thr Gly
            420                 425                 430

Leu Asp Cys Ile Arg Pro Cys Phe Trp Val Glu Leu Ile Arg Gly Arg
        435                 440                 445

Pro Lys Glu Asn Thr Ile Trp Thr Ser Gly Ser Ser Ile Ser Phe Cys
    450                 455                 460

Gly Val Asn Ser Asp Thr Val Gly Trp Ser Trp Pro Asp Gly Ala Glu
465                 470                 475                 480

Leu Pro Phe Thr Ile
                485
```

<210> SEQ ID NO 6
<211> LENGTH: 469
<212> TYPE: PRT
<213> ORGANISM: Influenza A virus
<220> FEATURE:
<223> OTHER INFORMATION: Mut D -continued

<400> SEQUENCE: 6

Met Asn Pro Asn Gln Lys Ile Ile Thr Ile Gly Ser Val Cys Met Thr
1 5 10 15

Ile Gly Met Ala Asn Leu Ile Leu Gln Ile Gly Asn Ile Ile Ser Ile
20 25 30

Trp Ile Ser His Ser Ile Gln Leu Gly Asn Gln Asn Gln Ile Glu Thr
35 40 45

Cys Asn Gln Ser Val Ile Thr Tyr Glu Asn Asn Thr Trp Val Asn Gln
50 55 60

Thr Tyr Val Asn Ile Ser Asn Thr Asn Phe Ala Ala Gly Gln Ser Val
65 70 75 80

Val Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

Ile Gly Ile Ser Gly Pro Asp Asn Gly Ala Val Ala Val Leu Lys Tyr
195 200 205

Asn Gly Ile Ile Thr Asp Thr Ile Lys Ser Trp Arg Asn Asn Ile Leu
210 215 220

Arg Thr Gln Glu Ser Glu Cys Ala Cys Val Asn Gly Ser Cys Phe Thr
225 230 235 240

Val Met Thr Asp Gly Pro Ser Asn Gly Gln Ala Ser Tyr Lys Ile Phe
245 250 255

Arg Ile Glu Lys Gly Lys Ile Val Lys Ser Val Glu Met Asn Ala Pro
260 265 270

Asn Tyr His Tyr Glu Glu Cys Ser Cys Tyr Pro Asp Ser Ser Glu Ile
275 280 285

Thr Cys Val Cys Arg Asp Asn Trp His Gly Ser Asn Arg Pro Trp Val
290 295 300

Ser Phe Asn Gln Asn Leu Glu Tyr Gln Ile Gly Tyr Ile Cys Ser Gly
305 310 315 320

Ile Phe Gly Asp Asn Pro Arg Pro Asn Asp Lys Thr Gly Ser Cys Gly
325 330 335

Pro Val Ser Ser Asn Gly Ala His Gly Val Lys Gly Phe Ser Phe Lys
340 345 350

Tyr Gly Asn Gly Val Trp Ile Gly Arg Thr Lys Ser Ile Ser Ser Arg
355 360 365

Asn Gly Phe Glu Met Ile Trp Asp Pro Asn Gly Trp Thr Gly Thr Asp
370 375 380

Asn Asn Phe Ser Ile Lys Gln Asp Ile Val Gly Ile Asn Glu Trp Ser
385 390 395 400

Gly Tyr Ser Gly Ser Phe Val Gln His Pro Glu Leu Thr Gly Leu Asp
405 410 415

-continued

```
Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 7
<211> LENGTH: 469
<212> TYPE: PRT
<213> ORGANISM: Influenza A virus
<220> FEATURE:
<223> OTHER INFORMATION: Mut E

<400> SEQUENCE: 7

Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Asn Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Val Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300
```

-continued

Ser Phe Asn Gln Asn Leu Glu Tyr Gln Ile Gly Tyr Ile Cys Ser Gly
305 310 315 320

Ile Phe Gly Asp Asn Pro Arg Pro Asn Asp Lys Thr Gly Ser Cys Gly
325 330 335

Pro Val Ser Ser Asn Gly Ala Asn Gly Val Lys Gly Phe Ser Phe Lys
340 345 350

Tyr Gly Asn Gly Val Trp Ile Gly Arg Thr Lys Ser Glu Asp Ser Arg
355 360 365

Asn Gly Phe Glu Met Ile Trp Asp Pro Asn Gly Trp Thr Gly Thr Asp
370 375 380

Asn Asn Phe Ser Ile Lys Gln Asp Ile Val Gly Ile Asn Glu Trp Ser
385 390 395 400

Gly Tyr Ser Gly Ser Phe Val Gln His Pro Glu Leu Thr Gly Leu Asp
405 410 415

Cys Ile Arg Pro Cys Phe Trp Val Glu Leu Ile Arg Gly Arg Pro Lys
420 425 430

Glu Asn Thr Ile Trp Thr Ser Gly Ser Ser Ile Ser Phe Cys Gly Val
435 440 445

Asn Ser Asp Thr Val Gly Trp Ser Trp Pro Asp Gly Ala Glu Leu Pro
450 455 460

Phe Thr Ile Asp Lys
465

<210> SEQ ID NO 8
<211> LENGTH: 469
<212> TYPE: PRT
<213> ORGANISM: Influenza A virus
<220> FEATURE:
<223> OTHER INFORMATION: Mut F

<400> SEQUENCE: 8

Met Asn Pro Asn Gln Lys Ile Ile Thr Ile Gly Ser Val Cys Met Thr
1 5 10 15

Ile Gly Met Ala Asn Leu Ile Leu Gln Ile Gly Asn Ile Ile Ser Ile
20 25 30

Trp Ile Ser His Ser Ile Gln Leu Gly Asn Gln Asn Gln Ile Glu Thr
35 40 45

Cys Asn Gln Ser Val Ile Thr Tyr Glu Asn Asn Thr Trp Val Asn Gln
50 55 60

Thr Tyr Val Asn Ile Ser Asn Thr Asn Phe Ala Ala Gly Gln Ser Val
65 70 75 80

Val Ser Val Lys Leu Ala Gly Asn Ser Ser Leu Cys Pro Val Ser Gly
85 90 95

Trp Ala Ile Tyr Ser Lys Asp Asn Ser Val Arg Ile Gly Ser Lys Gly
100 105 110

Asp Val Phe Val Ile Arg Glu Pro Phe Ile Ser Cys Ser Pro Leu Glu
115 120 125

Cys Arg Thr Phe Phe Leu Thr Gln Gly Ala Leu Leu Asn Asp Lys His
130 135 140

Ser Asn Gly Thr Ile Lys Asp Arg Ser Pro Tyr Arg Thr Leu Met Ser
145 150 155 160

Cys Pro Ile Gly Glu Val Pro Ser Pro Tyr Asn Ser Arg Phe Glu Ser
165 170 175

Val Ala Trp Ser Ala Ser Ala Cys His Asp Gly Ile Asn Trp Leu Thr
180 185 190

-continued

```
Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Asn Ile Leu
    210                 215                 220

Arg Thr Gln Glu Ser Glu Cys Ala Cys Val Asn Gly Ser Cys Phe Thr
225                 230                 235                 240

Val Met Thr Asp Gly Pro Ser Asn Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335

Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Thr Ala Ser Arg
        355                 360                 365

Asn Gly Phe Glu Met Ile Trp Asp Pro Asn Gly Trp Thr Gly Thr Asp
    370                 375                 380

Asn Asn Phe Ser Ile Lys Gln Asp Ile Val Gly Ile Asn Glu Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465


<210> SEQ ID NO 9
<211> LENGTH: 448
<212> TYPE: PRT
<213> ORGANISM: Influenza A virus
<220> FEATURE:
<223> OTHER INFORMATION: gi145284409 gbABP52008.1 neuraminidase

<400> SEQUENCE: 9

Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80
```

-continued

```
Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190

Thr Asp Thr Ile Lys Ser Trp Arg Asn Asn Ile Leu Arg Thr Gln Glu
        195                 200                 205

Ser Glu Cys Ala Cys Val Asn Gly Ser Cys Phe Thr Val Met Thr Asp
    210                 215                 220

Gly Pro Ser Asn Gly Gln Ala Ser His Lys Ile Phe Lys Met Glu Lys
225                 230                 235                 240

Gly Lys Val Val Lys Ser Val Glu Leu Asp Ala Pro Asn Tyr His Tyr
                245                 250                 255

Glu Glu Cys Ser Cys Tyr Pro Asn Ala Gly Glu Ile Thr Cys Val Cys
            260                 265                 270

Arg Asp Asn Trp His Gly Ser Asn Arg Pro Trp Val Ser Phe Asn Gln
        275                 280                 285

Asn Leu Glu Tyr Gln Ile Gly Tyr Ile Cys Ser Gly Val Phe Gly Asp
    290                 295                 300

Asn Pro Arg Pro Asn Asp Gly Thr Gly Ser Cys Gly Pro Val Ser Ser
305                 310                 315                 320

Asn Gly Ala Tyr Gly Val Lys Gly Phe Ser Phe Lys Tyr Gly Asn Gly
                325                 330                 335

Val Trp Ile Gly Arg Thr Lys Ser Thr Asn Ser Arg Ser Gly Phe Glu
            340                 345                 350

Met Ile Trp Asp Pro Asn Gly Trp Thr Glu Thr Asp Ser Ser Phe Val
        355                 360                 365

Lys Gln Asp Ile Val Ala Ile Thr Asp Trp Ser Gly Tyr Ser Gly Ser
    370                 375                 380

Phe Val Gln His Pro Glu Leu Thr Gly Leu Asp Cys Ile Arg Pro Cys
385                 390                 395                 400

Phe Trp Val Glu Leu Ile Arg Gly Arg Pro Lys Glu Ser Thr Ile Trp
                405                 410                 415

Thr Ser Gly Ser Ser Ile Ser Phe Cys Gly Val Asn Ser Asp Thr Val
            420                 425                 430

Gly Trp Ser Trp Pro Asp Gly Ala Glu Leu Pro Phe Thr Ile Asp Lys
        435                 440                 445
```

<210> SEQ ID NO 10
<211> LENGTH: 467
<212> TYPE: PRT
<213> ORGANISM: Influenza A virus
<220> FEATURE:
<223> OTHER INFORMATION: gi|94481616|gb|ABF21339.1| neuraminidase

<400> SEQUENCE: 10

Met Asn Pro Asn Gln Lys Ile Ile Thr Ile Gly Ser Val Ser Leu Thr
1 5 10 15

Ile Ala Thr Ile Cys Phe Leu Met Gln Ile Ala Ile Leu Val Thr Thr
20 25 30

Val Thr Leu His Phe Lys Gln Tyr Glu Cys Asp Ser Pro Ala Asn Asn
35 40 45

Gln Val Met Pro Cys Pro Ile Ile Ile Glu Arg Asn Ile Thr Glu Ile
50 55 60

Val Tyr Leu Thr Asn Thr Thr Ile Glu Lys Glu Ile Cys Pro Lys Leu
65 70 75 80

Val Glu Tyr Arg Asn Trp Ser Lys Pro Gln Cys Lys Ile Thr Gly Phe
85 90 95

Ala Pro Phe Ser Lys Asp Asn Ser Ile Arg Leu Ser Ala Gly Gly Asp
100 105 110

Ile Trp Val Thr Arg Glu Pro Tyr Val Ser Cys Asp Pro Gly Lys Cys
115 120 125

Tyr Gln Phe Ala Leu Gly Gln Gly Thr Thr Leu Asp Asn Lys His Ser
130 135 140

Asn Asp Thr Ile His Asp Arg Thr Pro His Arg Thr Leu Leu Met Asn
145 150 155 160

Glu Gly Val Pro Phe His Leu Gly Thr Arg Gln Val Cys Ile Ala Trp
165 170 175

Ser Ser Ser Ser Cys His Asp Gly Lys Ala Trp Leu His Val Cys Val
180 185 190

Thr Gly Tyr Asp Lys Asn Ala Thr Ala Ser Phe Ile Tyr Asp Gly Arg
195 200 205

Leu Val Asp Ser Ile Gly Ser Trp Ser Gln Asn Ile Leu Arg Thr Gln
210 215 220

Glu Ser Glu Cys Val Cys Ile Asn Gly Thr Cys Thr Val Val Met Thr
225 230 235 240

Asp Gly Ser Ala Ser Gly Arg Ala Asp Thr Lys Ile Leu Phe Ile Glu
245 250 255

Glu Gly Lys Ile Val His Ile Ser Pro Leu Ser Gly Ser Ala Gln His
260 265 270

Val Glu Glu Cys Ser Cys Tyr Pro Arg Tyr Pro Gly Val Arg Cys Ile
275 280 285

Cys Arg Asp Asn Trp Lys Gly Ser Asn Arg Pro Val Val Asp Ile Asn
290 295 300

Val Lys Asp Tyr Ser Ile Asp Ser Ser Tyr Val Cys Ser Gly Leu Val
305 310 315 320

Gly Asp Thr Pro Arg Asn Asn Asp Arg Ser Ser Asn Ser Tyr Cys Arg
325 330 335

Asn Pro Asn Asn Glu Lys Gly Asn His Gly Val Lys Gly Trp Ala Phe
340 345 350

Asp Asp Gly Asn Asp Val Trp Met Gly Arg Thr Ile Ser Glu Asp Ser
355 360 365

Arg Ser Gly Tyr Glu Thr Phe Lys Val Ile Gly Gly Trp Ser Thr Pro
370 375 380

Asn Ser Lys Leu Gln Ile Asn Arg Gln Val Ile Val Asp Ser Asp Asn
385 390 395 400

Arg Ser Gly Tyr Ser Gly Ile Phe Ser Val Glu Gly Lys Ser Cys Ile
405 410 415

-continued

```
Asn Arg Cys Phe Tyr Val Glu Leu Ile Arg Gly Arg Glu Gln Glu Thr
            420                 425                 430

Arg Val Trp Trp Thr Ser Asn Ser Ile Val Val Phe Cys Gly Thr Ser
        435                 440                 445

Gly Thr Tyr Gly Thr Gly Ser Trp Pro Asp Gly Ala Asp Ile Asn Leu
    450                 455                 460

Met Pro Ile
465


<210> SEQ ID NO 11
<211> LENGTH: 465
<212> TYPE: PRT
<213> ORGANISM: Influenza A virus
<220> FEATURE:
<223> OTHER INFORMATION: gi|496493393|gb|AGL44440.1| neuraminidase

<400> SEQUENCE: 11

Met Asn Pro Asn Gln Lys Ile Leu Cys Thr Ser Ala Thr Ala Ile Ile
1               5                   10                  15

Ile Gly Ala Ile Ala Val Leu Ile Gly Met Ala Asn Leu Gly Leu Asn
            20                  25                  30

Ile Gly Leu His Leu Lys Pro Gly Cys Asn Cys Ser His Ser Gln Pro
        35                  40                  45

Glu Thr Thr Asn Thr Ser Gln Thr Ile Ile Asn Asn Tyr Tyr Asn Glu
    50                  55                  60

Thr Asn Ile Thr Asn Ile Gln Met Glu Glu Arg Thr Ser Arg Asn Phe
65                  70                  75                  80

Asn Asn Leu Thr Lys Gly Leu Cys Thr Ile Asn Ser Trp His Ile Tyr
                85                  90                  95

Gly Lys Asp Asn Ala Val Arg Ile Gly Glu Ser Ser Asp Val Leu Val
            100                 105                 110

Thr Arg Glu Pro Tyr Val Ser Cys Asp Pro Asp Glu Cys Arg Phe Tyr
        115                 120                 125

Ala Leu Ser Gln Gly Thr Thr Ile Arg Gly Lys His Ser Asn Gly Thr
    130                 135                 140

Ile His Asp Arg Ser Gln Tyr Arg Ala Leu Ile Ser Trp Pro Leu Ser
145                 150                 155                 160

Ser Pro Pro Thr Val Tyr Asn Ser Arg Val Glu Cys Ile Gly Trp Ser
                165                 170                 175

Ser Thr Ser Cys His Asp Gly Lys Ser Arg Met Ser Ile Cys Ile Ser
            180                 185                 190

Gly Pro Asn Asn Asn Ala Ser Ala Val Val Trp Tyr Asn Arg Arg Pro
        195                 200                 205

Val Ala Glu Ile Asn Thr Trp Ala Arg Asn Ile Leu Arg Thr Gln Glu
    210                 215                 220

Ser Glu Cys Val Cys His Asn Gly Val Cys Pro Val Val Phe Thr Asp
225                 230                 235                 240

Gly Ser Ala Thr Gly Pro Ala Asp Thr Arg Ile Tyr Tyr Phe Lys Glu
                245                 250                 255

Gly Lys Ile Leu Lys Trp Glu Ser Leu Thr Gly Thr Ala Lys His Ile
            260                 265                 270

Glu Glu Cys Ser Cys Tyr Gly Glu Arg Thr Gly Ile Thr Cys Thr Cys
        275                 280                 285

Arg Asp Asn Trp Gln Gly Ser Asn Arg Pro Val Ile Gln Ile Asp Pro
    290                 295                 300
```

-continued

```
Val Ala Met Thr His Thr Ser Gln Tyr Ile Cys Ser Pro Val Leu Thr
305                 310                 315                 320

Asp Asn Pro Arg Pro Asn Asp Pro Asn Ile Gly Lys Cys Asn Asp Pro
                325                 330                 335

Tyr Pro Gly Asn Asn Asn Asn Gly Val Lys Gly Phe Ser Tyr Leu Asp
            340                 345                 350

Gly Ala Asn Thr Trp Leu Gly Arg Thr Ile Ser Thr Ala Ser Arg Ser
        355                 360                 365

Gly Tyr Glu Met Leu Lys Val Pro Asn Ala Leu Thr Asp Asp Arg Ser
    370                 375                 380

Lys Pro Ile Gln Gly Gln Thr Ile Val Leu Asn Ala Asp Trp Ser Gly
385                 390                 395                 400

Tyr Ser Gly Ser Phe Met Asp Tyr Trp Ala Glu Gly Asp Cys Tyr Arg
                405                 410                 415

Ala Cys Phe Tyr Val Glu Leu Ile Arg Gly Arg Pro Lys Glu Asp Lys
            420                 425                 430

Val Trp Trp Thr Ser Asn Ser Ile Val Ser Met Cys Ser Ser Thr Glu
        435                 440                 445

Phe Leu Gly Gln Trp Asn Trp Pro Asp Gly Ala Lys Ile Glu Tyr Phe
    450                 455                 460

Leu
465
```